US011066678B2

(12) United States Patent
Van Der Loo et al.

(10) Patent No.: US 11,066,678 B2
(45) Date of Patent: Jul. 20, 2021

(54) METHODS OF IMPROVING TITER IN TRANSFECTION-BASED PRODUCTION SYSTEMS USING EUKARYOTIC CELLS

(71) Applicant: CHILDREN'S HOSPITAL MEDICAL CENTER, Cincinnati, OH (US)

(72) Inventors: Johannes Van Der Loo, Loveland, OH (US); Punam Malik, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 14/905,713

(22) PCT Filed: Jul. 18, 2014

(86) PCT No.: PCT/US2014/047211
§ 371 (c)(1),
(2) Date: Jan. 15, 2016

(87) PCT Pub. No.: WO2015/010030
PCT Pub. Date: Jan. 22, 2015

(65) Prior Publication Data
US 2016/0168590 A1    Jun. 16, 2016

Related U.S. Application Data

(60) Provisional application No. 61/847,897, filed on Jul. 18, 2013.

(51) Int. Cl.
*C12N 15/86* (2006.01)
*C12N 7/00* (2006.01)
(52) U.S. Cl.
CPC ............... *C12N 15/86* (2013.01); *C12N 7/00* (2013.01); *C12N 2740/10043* (2013.01); *C12N 2740/10051* (2013.01); *C12N 2740/13051* (2013.01); *C12N 2740/16051* (2013.01)
(58) Field of Classification Search
None
See application file for complete search history.

(56) References Cited

U.S. PATENT DOCUMENTS

| 6,805,730 | B2 | 10/2004 | Herczeg |
| 7,575,911 | B2 | 8/2009 | Silber et al. |
| 9,551,010 | B2 * | 1/2017 | Van der Loo .......... C12N 15/63 |
| 2010/0035342 | A1 | 2/2010 | Cheng et al. |
| 2011/0294114 | A1 | 12/2011 | Van Der Loo et al. |
| 2012/0264688 | A1 | 10/2012 | Hinderer et al. |
| 2013/0302898 | A1 | 11/2013 | Van der Loo et al. |

FOREIGN PATENT DOCUMENTS

| EP | 1869171 B1 | 10/2008 |
| WO | 03039459 A2 | 5/2003 |
| WO | 2008069902 A2 | 6/2008 |

OTHER PUBLICATIONS

Yamada et al., Biotechniques, 2003, 34:1074-1080.*
Cooper et al., Journal of Virology Methods, Oct. 2011, 177(1):1-9.*
KrosFlo Research II TFF System, Product Information and Operating Instructions, 2000.*
Zufferey et al., "Self-inactivating lentivirus vector for safe and efficient in vivo gene delivery," Journal of Virology, 72(12). pp. 9873-9880. Dec. 1998.
Zychilnski et al., "Physiological promoters reduce the genotoxic risk of integrating gene vectors," Molecular Therapy, 16(4). pp. 718-725. Apr. 2008. Published ahead of print Mar. 4, 2008.
Baum et al., "Novel retroviral vectors for efficient expression of the multidrug resistance (mdr-1) gene in early hematopoietic cells," Journal of Virology, 69(12). pp. 7541-7547. Dec. 1995.
Boussif et al., "A versatile vector for gene and oligonucleotide transfer into cells in culture and in vivo: polyethylenimine," Proceedings of the National Academy of Sciences of the United States of America, 92(16). pp. 7297-7301. Aug. 1, 1995.
Cornetta et al., "Retroviral vector production in the National Gene Vector Laboratory at Indiana University," Gene Therapy, 12(Suppl. 1). pp. S28-S35. Oct. 2005.
Dull et al., "A third-generation lentivirus vector with a conditional packaging system," Journal of Virology, 72(11). pp. 8463-8471. Nov. 1998.
Felgner et al., "Lipofection: a highly efficient, lipid-mediated DNA-transfection procedure," Proceedings of the National Academy of Sciences of the United States of America, 84(21). pp. 7413-7417. Nov. 1, 1987.
Feng et al., "Construction of eukaryotic expression plasmid of human PRX3 and its expression in HEK-293FT cells," Journal of Huazhong University of Science and Technology [Medical Sciences], 24(4). pp. 311-313. Aug. 2004.
Garaerts et al., "Upscaling of lentiviral vector production by tangential flow filtration," The Journal of Gene Medicine, 7(10). pp. 1299-1310. Oct. 2005. Published ahead of print May 20, 2005.
Graham et al., "A new technique for the assay of infectivity of human adenovirus 5 DNA," Virology, 52(2). pp. 456-467. Apr. 1973.
Grez et al., "Embryonic stem cell virus, a recombinant murine retrovirus with expression in embryonic stem cells," Proceedings of the National Academy of Sciences of the United States of America, 87(23). pp. 9202-9206. Dec. 1, 1990.
Hacein-Bey-Abina et al., "LMO2-associated clonal T cell proliferation in two patients after gene therapy for SCID-X1," Science, 32(5644). pp. 415-419. Oct. 17, 2003.
Hanenberg et al., "Colocalization of retrovirus and target cells on specific fibronectin fragments increases genetic transduction of mammalian cells," Nature Medicine, 2(8). pp. 876-882. Aug. 1996.
Herbst et al., "10-year stability of clinical-grade serum-free ?-retroviral vector-containing medium" Gene Therapy, 18(2). pp. 210-212. Feb. 2011. Published ahead of print Nov. 11, 2010.

(Continued)

*Primary Examiner* — Nicole Kinsey White
(74) *Attorney, Agent, or Firm* — McDermott Will & Emery LLP

(57) ABSTRACT

The invention relates to methods of improving titer in transfection-based bioreactor culture production or transfection-based production systems using eukaryotic cells.

14 Claims, 14 Drawing Sheets

(56) References Cited

OTHER PUBLICATIONS

Higashikawa et al., "Kinetic analyses of stability of simple and complex retroviral vectors," Virology, 280(1). pp. 124-131. Feb. 1, 2001.

Hildinger et al., "Design of 5' untranslated sequences in retroviral vectors developed for medical use," Journal of Virology, 73(5). pp. 4083-4089. May 1999.

Howe et al., "Insertional mutagenesis combined with acquired somatic mutations causes leukemogenesis following gene therapy of SCID-X1 patients," The Journal of Clinical Investigation, 118(9). pp. 3143-3150. Sep. 2, 2008. Published ahead of print Aug. 7, 2008.

International Search Report and Written Opinion in International Patent Application No. PCT/US2014/047211, dated Dec. 12, 2014. 11 pages.

Jordan et al., "Transfection of adherent and suspended cells by calcium phosphate," Methods, 33(2). pp. 136-143. Jun. 2004.

Karolewski et al., "Comparison of transfection conditions for a lentivirus vector produced in large volumes," Human Gene Therapy, 14(14). pp. 1287-1296. Sep. 20, 2003.

Kraunus et al., "Self-inactivating retroviral vectors with improved RNA processing," Gene Therapy, 11(21). pp. 1568-1578. Nov. 2004. Published ahead of print Sep. 16, 2004.

Loew et al., "A new PG13-based packaging cell line for stable production of clinical-grade self-inactivating gamma-retroviral vectors using targeted integration," Gene Therapy, 17(2). pp. 272-280. Feb. 2010. Published ahead of print Oct. 29, 2009.

Merten et al., "Comparison of different bioreactor systems for the production of high titer retroviral vectors," Biotechnology Progress, 17(2). pp. 326-335. Mar. 2001.

Merten et al., "Large-scale manufacture and characterization of a lentiviral vector produced for clinical ex vivo gene therapy application," Human Gene Therapy, 22(3). pp. 343-356. Mar. 7, 2011.

Merten, "State-of-the-art of the production of retroviral vectors," The Journal of Gene Medicine, 6(S1). pp. S105-S124. Feb. 2004.

Modlich et al., "Cell-culture assays reveal the importance of retroviral vector design for insertional genotoxicity," Blood, 108(8). pp. 2545-2553. Oct. 15, 2006. Published ahead of print Jul. 6, 2006.

Montini et al., "Hematopoietic stem cell gene transfer in a tumor-prone mouse model uncovers low genotoxicity of lentiviral vector integration," Nature Biotechnology, 24(6). pp. 687-696. Jun. 2006. Published ahead of print May 28, 2006.

Naldini et al., "Efficient transfer, integration, and sustained long-term expression of the transgene in adult rat brains injected with a lentiviral vector," Proceedings of the National Academy of Sciences of the United States of America, 93(21). pp. 11382-11388. Oct. 15, 1996.

Nordling et al., "Release testing of retroviral vectors and gene-modified cells," Methods in Molecular Biology, vol. 506, Chapter 18. pp. 265-279. 2009.

Peng, "Current status of gendicine in China: recombinant human Ad-p53 agent for treatment of cancers," Human Gene Therapy, 16(9). pp. 1016-1027. Sep. 8, 2005.

Persons et al., "Solving the problem of g-retroviral vectors containing long terminal repeats," Molecular Therapy, 19(2). pp. 229-231. Feb. 2011.

Pierce et al., "Scalability of a Disposable Bioreactor from 25 L-500 L Run in Perfusion Mode with a CHO-Based Cell Line: A Tech Review," Bioprocessing Journal, 3(4). pp. 51-56. Jul.-Aug. 2004.

Przybylowski et al., "Production scale-up and validation of packaging cell clearance of clinical-grade retroviral vector stocks produced in cell factories," Gene Therapy, 13(1). pp. 95-100. Jan. 2006. Published ahead of print Sep. 22, 2005.

Reeves et al., "Packaging cell line characteristics and optimizing retroviral vector titer: the National Gene Vector Laboratory experience," Human Gene Therapy, 11(15). pp. 2093-2103. Oct. 10, 2000.

Sastry et al., "Evaluation of plasmid DNA removal from lentiviral vectors by benzonase treatment," Human Gene Therapy, 15(2). pp. 221-226. Feb. 2004.

Schambach et al., "Design and production of retro- and lentiviral vectors for gene expression in hematopoietic cells," Methods in Molecular Biology, vol. 506, Chapter 14. pp. 191-205. 2009.

Schambach et al., "Equal potency of gammaretroviral and lentiviral SIN vectors for expression of O6-methylguanine-DNA methyltransferase in hematopoietic cells," Molecular Therapy, 13(2). pp. 391-400. Feb. 2006. Published ahead of print Oct. 12, 2005.

Schambach et al., "Improving transcriptional termination of self-inactivating gamma-retroviral and lentiviral vectors," Molecular Therapy, 15(6). pp. 1167-1173. Jun. 2007. Published ahead of print Apr. 3, 2007.

Schambach et al., "Overcoming promoter competition in packaging cells improves production of self-inactivating retroviral vectors," Gene Therapy, 13(21). pp. 1524-1533. Nov. 2006. Published ahead of print Jun. 8, 2006.

Schleef et al., "Animal-free production of ccc-supercoiled plasmids for research and clinical applications," Journal of Gene Medicine, 6(S1). pp. S45-S53. Feb. 2004.

Segura et al., "A novel purification strategy for retrovirus gene therapy vectors using heparin affinity chromatography," Biotechnology and Bioengineering, 90(4). pp. 391-404. May 20, 2005. Published ahead of print Apr. 5, 2005.

Segura et al., "Downstream processing of oncoretroviral and lentiviral gene therapy vectors," Biotechnology Advances, 24(3). pp. 321-337. May-Jun. 2006.

Segura et al., "Purification and characterization of retrovirus vector particles by rate zonal ultracentrifugation," Journal of Virological Methods, 133(1). pp. 82-91. Apr. 2006.

Thornhill et al., "Self-inactivating gammaretroviral vectors for gene therapy of X-linked severe combined immunodeficiency," Molecular Therapy, 16(3). pp. 590-598. Mar. 2008. Published ahead of print Jan. 8, 2008.

Throm et al., "Efficient construction of producer cell lines for a SIN lentiviral vector for SCID-X1 gene therapy by concatemeric array transfection," Blood, 113(21). pp. 5104-5110. May 21, 2009. Published ahead of print Mar. 13, 2009.

U.S. Department of Health and Human Services, Food and Drug Administration, Center for Biologics Evaluation and Research, "Guidance for human somatic cell therapy and gene therapy," Human Gene Therapy, 12(3). pp. 303-314. Feb. 10, 2001.

Wikström et al., "Clinical grade vector production: analysis of yield, stability, and storage of gmp-produced retroviral vectors for gene therapy," Biotechnology Progress, 20(4). pp.1198-1203. Jul.-Aug. 2004.

Williams et al., "Gene Therapy—New Challenges Ahead," Science, 302(5644). pp. 400-401. Oct. 17, 2003.

Wilson, "Gendicine: the first commercial gene therapy product," Human Gene Therapy, 16(9). pp. 1014-1015. Sep. 8, 2005.

Wright et al., "Transient transfection methods for clinical adeno-associated viral vector production," Human Gene Therapy, 20(7). pp. 698-706. Jul. 2009.

Wu et al., "Production of retrovirus and adenovirus vectors for gene therapy: a comparative study using microcarrier and stationary cell culture," Biotechnology Progress, 18(3). pp. 617-622. May-Jun. 2002.

Yu et al., "Self-inactivating retroviral vectors designed for transfer of whole genes into mammalian cells," Proceedings of the National Academy of Sciences of the United States of America, 83(10). pp. 3194-3198. May 1, 1986.

Ausubel et al., "Production of CGMP-Grade Lentiviral Vectors," BioProcess International 10(2):32-43, Feb. 2012.

* cited by examiner

Total Number and Cell Viability of Suspension-based 293F Cells

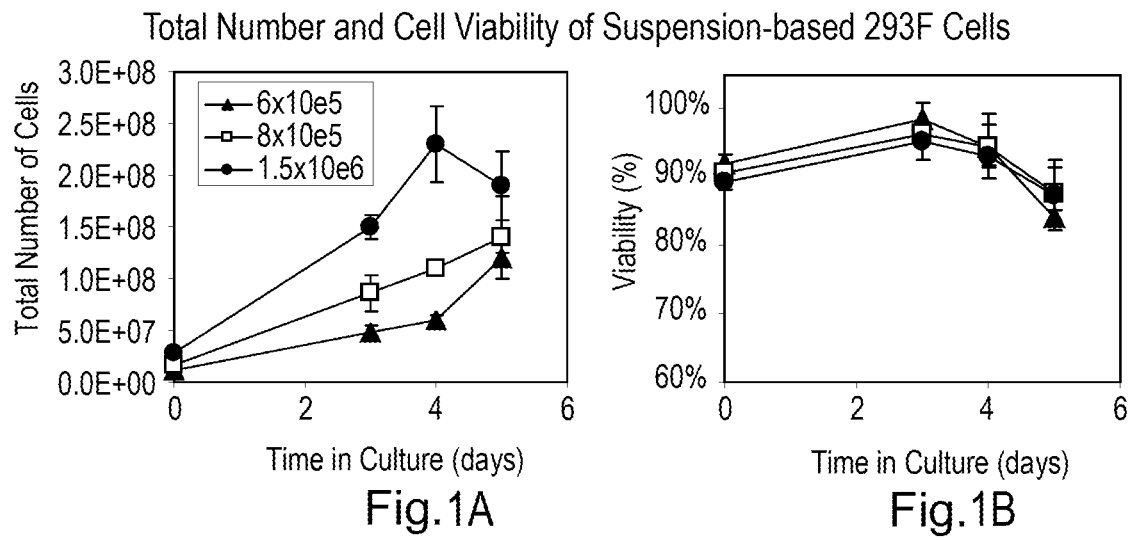

Titer of gamma-retroviral vector produced in adherent 293T or suspension 293F cells using three transfection methods (A) and relative titer of lentivirus and gamma-retrovirus (B)

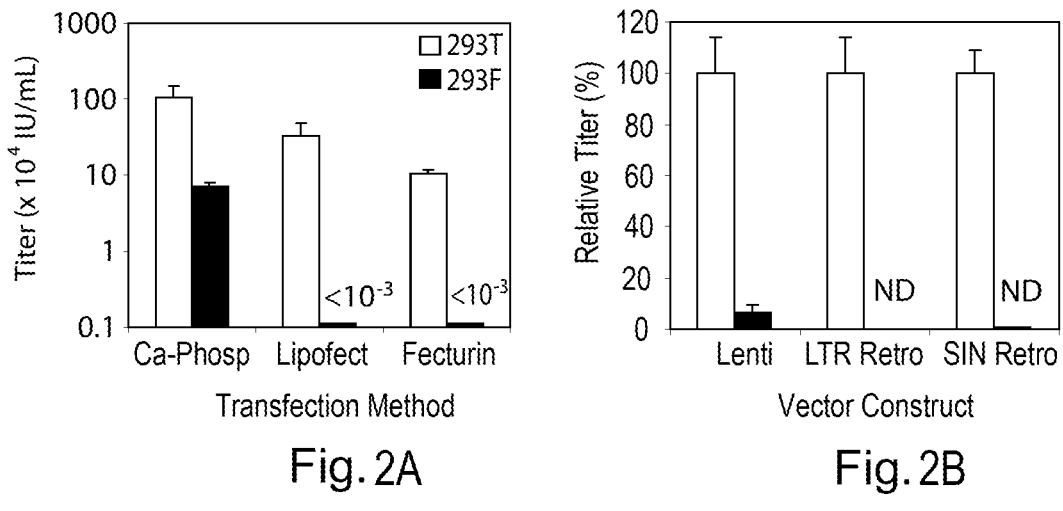

Titer of gamma-retroviral vector generated in the FibraStage Culture System

| Time of Transfection | Infectious Titer gamma-Retrovirus (x10⁵ IU/mL) | | | | |
|---|---|---|---|---|---|
| | Harvest 1 | Harvest 2 | Harvest 3 | Harvest 4 | Harvest 5 |
| 1 day post-seeding | <0.1 | <0.1 | <0.1 | <0.1 | <0.1 |
| 4 hours post-seeding | 4.3 | 2.4 | 1.8 | 1.2 | 0.4 |

Fig.3

Titer of gamma-Retroviral from 293T cells transfected with different amount of plasmid on Tissue-Culture Plastic (4A) and on FibraCel (4B)

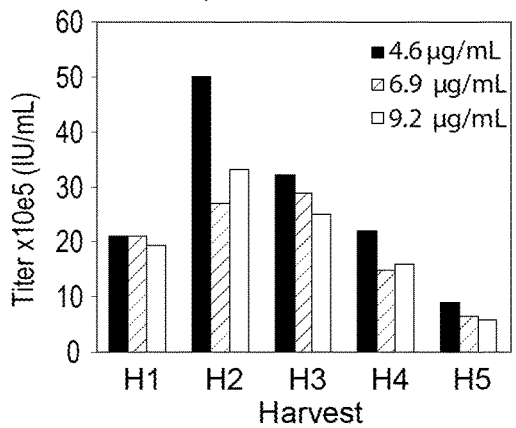

Fig.4A

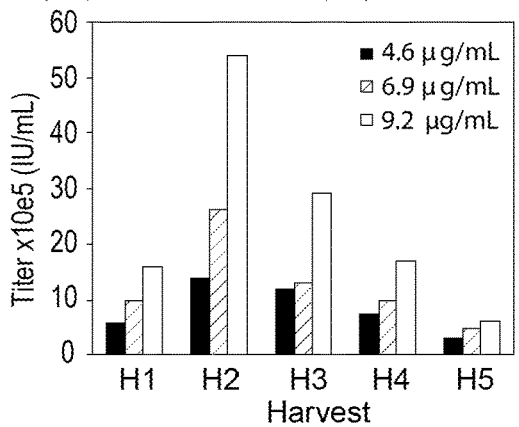

Fig.4B

Titer gamma-Retroviral vector generated from 293T cells plated at different cells densities

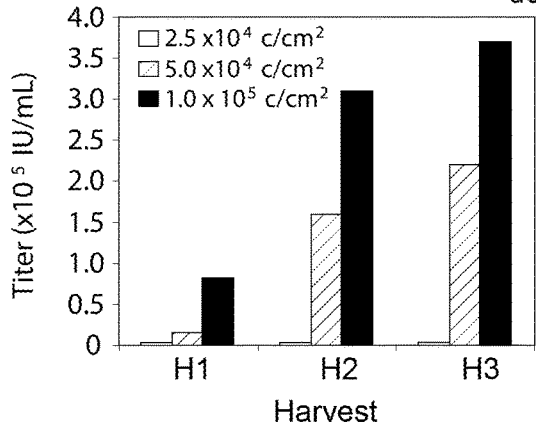

Fig.5A

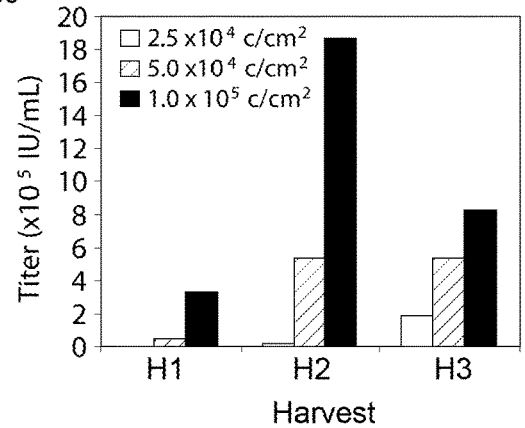

Fig.5B

Titer of gamma-Retroviral vector generated by transfection with media change at different time points (A), and with different exposure to TrypLESelect and PBS

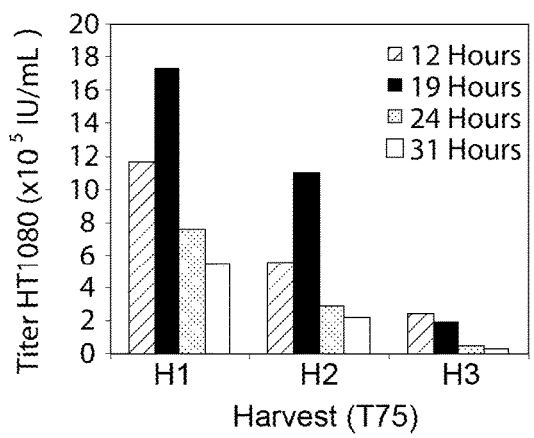

Fig.6A

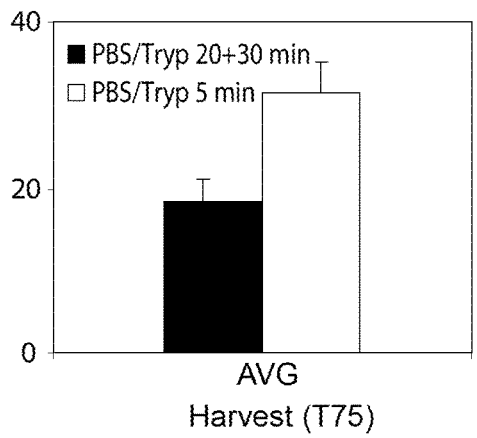

Fig.6B

| Arm | Seed on | Transfect on | Media Change With | Media Change on |
|---|---|---|---|---|
| 3 day cells 3 day CM | Friday | Monday | 50% 3-day CM | Tuesday |
| 3 day cells 4 day CM | Friday | Monday | 50% 4-day CM | Tuesday |
| 4 day cells 3 day CM | Friday | Tuesday | 50% 3-day CM | Wednesday |
| 4 day cells 4 day CM | Friday | Tuesday | 50% 4-day CM | Wednesday |

Experimental Design for Tangential Flow Filtration (TFF) Membrane Comparison and use of Bubbles

| Group | Membrane | Bubbles | Final Volume (mL) |
|---|---|---|---|
| 1 | Polysulfone (PS) | No | 10.2 |
| 2 | Polysulfone (PS) | Yes (0.5 mL) | 8.7 |
| 3 | Polyethersulfone (PES) | No | 10.0 |

# METHODS OF IMPROVING TITER IN TRANSFECTION-BASED PRODUCTION SYSTEMS USING EUKARYOTIC CELLS

CROSS-REFERENCE TO RELATED APPLICATIONS

The present application is a U.S. National Stage entry under 35 U.S.C. § 371 of International Application No. PCT/US2014/047211, filed on Jul. 18, 2014, designating the United States of America and published in English on Jan. 22, 2015, which in turn claims priority under 35 U.S.C. § 119(e) to U.S. Provisional Application No. 61/847,897, filed on Jul. 18, 2013, each of which is hereby incorporated by reference in its entirety.

FIELD OF THE INVENTION

The invention disclosed herein generally relates to methods of improving titer in transfection-based bioreactor culture production or transfection-based production systems using a eukaryotic cell.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Improvement of Viral Titer

Significant research has been devoted to improving viral titer by manipulating the parameters of production in closed system bioreactors or alternate large-scale culture systems. Increases in titer translate into practical benefits, including decreased costs and the related potential for expanding the patient base for clinical trials. Thus, there is a continued need in the art for improving titer by optimizing the parameters of bioreactor or alternate large-scale culture systems-based vector production.

SUMMARY OF THE INVENTION

Methods and compositions described herein are provided by way of example and should not in any way limit the scope of the invention.

In one aspect, a method of improving titer in a transfection-based production system using a eukaryotic cell is provided. The method can include at least one of: seeding eukaryotic at a cell density of at least $5 \times 10^4$ cells/cm$^2$ 4 to 5 days prior to cell harvest and transfection; harvesting of a confluent population of the cells that have progressed beyond log phase of growth for transfection; incubating transfection reagents at room temperature for 20 minutes before mixing with the population; transfecting the cells by mixing the population with the transfection reagents and plasmid DNA at the time of re-seeding the cells into a culture vessel; re-seeding the cells at a density of about $2.5 \times 10^5$ cells per square centimeter; re-feeding the cells with a culture media containing at least 50% conditioned media; capturing viral vectors from cell-free supernatant using an anion-exchange capsule, and concentrating captured viral vectors using a Polysulfone (PS) or Polyether (PES) tangential-flow filtration (TFF) module, where any of the seeding, harvesting, incubating, transfecting, re-seeding, re-feeding, capturing, and concentrating steps, alone or in any combination, results in an improved titer, by at least 2-fold, in a transfection-based production system.

In another aspect, a method of improving viral titer in a transfection-based production system using a eukaryotic cell is provided. The method can include at least one of: harvesting a confluent population of eukaryotic cells that have progressed beyond log phase of cell growth for at least 24 hours prior to transfection; transfecting the cells by mixing the population with transfection reagents and plasmid DNA at the time of re-seeding the cells into a culture vessel, where the harvesting and transfecting steps, alone or in combination, results in an improved viral titer, by at least 2-fold, in a transfection-based production using a eukaryotic cell.

In another aspect, a method of improving titer in transfection-based production using a eukaryotic cell is provided. The method can include at least one of: seeding eukaryotic cells at a cell density of at least $5 \times 10^4$ cells/cm$^2$ 4 to 5 days prior to cell harvest and transfection, harvesting a confluent population of the cells that have progressed beyond log phase of growth for transfection; and transfecting the cells by mixing the population with transfection reagents and plasmid DNA at the time of re-seeding the cells into a culture vessel, where any of the seeding, harvesting, and transfecting steps, alone or in any combination, results in an improved titer, by at least 2-fold, in transfection-based production using a eukaryotic cell.

In another aspect, a method of improving titer in transfection-based bioreactor culture production using a eukaryotic cell is provided. The method can include at least one of: seeding eukaryotic cells at a cell density of at least $5 \times 10^4$ cells/cm$^2$ 4 to 5 days prior to cell harvest and transfection; harvesting a confluent population of the cells that have progressed beyond log phase of growth for transfection; and transfecting the cells by mixing the population with transfection reagents and at least 9.2 µg/ml of plasmid DNA at the time of re-seeding the cells into a culture vessel; where any of the seeding, harvesting, and transfecting steps, alone or in any combination, results in an improved titer, by at least 2-fold, in transfection-based bioreactor culture production using a eukaryotic cell.

In another aspect, a method of improving titer in a transfection-based production system using a eukaryotic cell is provided. The method can include at least one of: seeding eukaryotic at a cell density of at least $5 \times 10^4$ cells/cm$^2$ 4 to 5 days prior to cell harvest and transfection; harvesting of a confluent population of the cells that have progressed beyond log phase of growth for transfection; transfecting the cells by mixing the population with transfection reagents and plasmid DNA at the time of re-seeding the cells into a culture vessel; re-seeding transfected cells at a density of about $2.5 \times 10^5$ cells per square centimeter, where any of the seeding, harvesting, transfecting, and re-seeding steps, alone or in any combination, results in an improved titer, by at least 2-fold, in a transfection-based production system.

In another aspect, a method of improving titer in a transfection-based production system using a eukaryotic cell is provided. The method can include at least one of: seeding eukaryotic at a cell density of at least $5 \times 10^4$ cells/cm$^2$ 4 to 5 days prior to cell harvest and transfection; harvesting of a confluent population of the cells that have progressed beyond log phase of growth for transfection; transfecting the cells by mixing the population with transfection reagents and plasmid DNA at the time of re-seeding the cells into a culture vessel; re-seeding the cells at a density of about $2.5\times10^5$ cells per square centimeter; re-feeding the cells with a culture media containing at least 50% conditioned media; where any of the seeding, harvesting, transfecting, re-seeding and re-feeding steps, alone or in any combination, results in an improved titer, by at least 2-fold, in a transfection-based production system.

In another aspect, a method of improving titer in a transfection-based production system using a eukaryotic cell is provided. The method can include at least one of: seeding eukaryotic at a cell density of at least $5\times10^4$ cells/cm$^2$ 4 to 5 days prior to cell harvest and transfection; harvesting of a confluent population of the cells that have progressed beyond log phase of growth for transfection; incubating transfection reagents at room temperature for 20 minutes before mixing with the population; transfecting the cells by mixing the population with the transfection reagents and plasmid DNA at the time of re-seeding the cells into a culture vessel; re-seeding the cells at a density of about $2.5\times10^5$ cells per square centimeter; re-feeding the cells with a culture media containing at least 50% conditioned media; where any of the seeding, harvesting, incubating, transfecting, re-seeding and re-feeding steps, alone or in any combination, results in an improved titer, by at least 2-fold, in a transfection-based production system.

In another aspect, a method of improving titer in a transfection-based production system using a eukaryotic cell is provided. The method can include at least one of: seeding eukaryotic at a cell density of at least $5\times10^4$ cells/cm$^2$ 4 to 5 days prior to cell harvest and transfection; harvesting of a confluent population of the cells that have progressed beyond log phase of growth for transfection; incubating transfection reagents at room temperature for 20 minutes before mixing with the population; transfecting the cells by mixing the population with the transfection reagents and plasmid DNA at the time of re-seeding the cells into a culture vessel; re-seeding the cells at a density of about $2.5\times10^5$ cells per square centimeter; re-feeding the cells with a culture media containing at least 50% conditioned media; and capturing viral vectors from cell-free supernatant using an anion-exchange capsule, where any of the seeding, harvesting, incubating, transfecting, re-seeding, re-feeding, and capturing steps, alone or in any combination, results in an improved titer, by at least 2-fold, in a transfection-based production system.

In some embodiments of the methods, the culture vessel can be treated with poly-L-lysine before use. In some embodiments, the culture vessel can be a 5-layer cell stack vessel. In some embodiments, the plasmid DNA can include a viral vector and at least one of a plasmid encoding a viral Gag/Pol gene, a plasmid encoding a viral Envelop gene and a plasmid encoding a viral Rev gene. In some embodiments, the viral vector can be a lentiviral vector.

In some embodiments, the methods can further include gassing the culture vessel with 5% $CO_2$ or a mixture of 5% $CO_2$ and 40% $O_2$ for 30 seconds after each post-transfecting step before placing the culture vessel into an incubator.

In some embodiments, the anion-exchange capsule can be sanitized with 1 Molar NaOH, pre-conditioned with 1 Molar NaCl, and equilibrated with 25 mMolar Tris-HCl (pH 8.0), 150 mMolar NaCl prior to viral capture. In some embodiments, the anion-exchange capsule can be rinsed with 25 mMolar Tris-HCl (pH 8.0), 150 mMolar NaCl after viral capture. In some embodiments, the anion-exchange capsule can be rinsed with 25 mMolar Tris-HCl (pH 8.0), 1.2 M NaCl to elute captured viral vector.

In some embodiments, the concentrating step can include applying a trans-membrane pressure of 5-6 psi to the TFF module. In some embodiments, the concentrating step can include applying a shear of 5000 to 6000 s$^{-1}$ to the TFF module. In some embodiments, the concentrating step can include introducing air into the TFF module before collecting concentrated viral vectors.

BRIEF DESCRIPTION OF THE FIGURES

Those of skill in the art will understand that the drawings, described below, are for illustrative purposes only. The drawings are not intended to limit the scope of the present teachings in any way.

FIG. 1 depicts the expansion total number (A) and cell viability (B) of 293F cell suspension culture over time when initiated at $6\times10^5$, $8\times10^5$, and $1.5\times10^6$ c/mL; mean±SD (n=3).

FIG. 2 depicts titer of gamma-retroviral vector, MIEG3 (RD114-pseudotyped) produced on adherent 293T and suspension 293F cells, transfected using different transfection methods (A) and relative titer of a lentivirus and gamma-retrovirus (LTR and SIN configuration) in 293T and 293F cells transfected with LIPOFECTAMINE™ (transfection reagent) (B); mean±SD (n=2). ND, not detected.

FIG. 3 depicts titer of gamma-retroviral vector generated from 293T cells ($2.5\times10^8$) transfected in a 500 mL FIBRASTAGE™ culture system (New Brunswick Scientific; disposable 500 mL bottle with FIBRA-CEL® (solid support cell growth matrix) mounted on a movable stage) with 500 microgram of SRS11.SF.GFP.pre*SE, 450 microgram of pCDNA3.MLV.g/p and 200 microgram of GALV envelope plasmid using Calcium Phosphate. One group was transfected at the time of seeding (4 hours post-seeding), the other group was transfected the day after seeding.

FIG. 4 depicts titer of gamma-retroviral vector generated from 293T cells transfected on tissue culture plastic ($2\times10^7$ cells per T75 in 10 mL D10) (A) or on FIBRA-CEL® (solid support cell growth matrix) ($2\times10^8$ cells per 2 gram in 100 mL D10) (B) with SRS11.SF.DsRed2.pre*, pCDNA3.MLV.gp, and Eco-env using different amounts of plasmid DNA (total amount expressed as µg per mL of media). Vector was harvested at 12-hour intervals and titered on NIH 3T3.

FIG. 5 depicts titer of gamma-retroviral vector generated from 293T cells plated at cell densities of $2.5\times10^4$, $5\times10^4$, and $1\times10^5$ cells/cm$^2$ 4 days prior to transfection. At the day of transfection, cells were harvested and $2\times10^8$ cells from each group were transfected with a GALV pseudotyped SIN11.SF.eGFP.pre* (A) and SRS11.EFS.IL2RGpre* (B). Vector was harvested at 12-hour intervals and titered on HT1080.

FIG. 6 depicts titer of gamma-retroviral vector generated from 293T cells transfected T75 ($2\times10^7$ cells per flask in 10 mL D10) with SERS11.EGFP.pre*, pCDNA3.MLV.gp, and GALV-env. Post-transfection, media was changed at various time points (A). Comparison of PBS rinse followed by 5 min exposure of TRYPLE™ SELECT (animal origin-free recombinant cell-dissociation enzyme) and exposure to PBS for 20 min and exposure to TRYPLE™ SELECT (animal origin-free recombinant cell-dissociation enzyme) for 30 min, all groups showed >95% viability (B). Average ±SD (n=2).

DESCRIPTION OF THE INVENTION

Figure 7A:
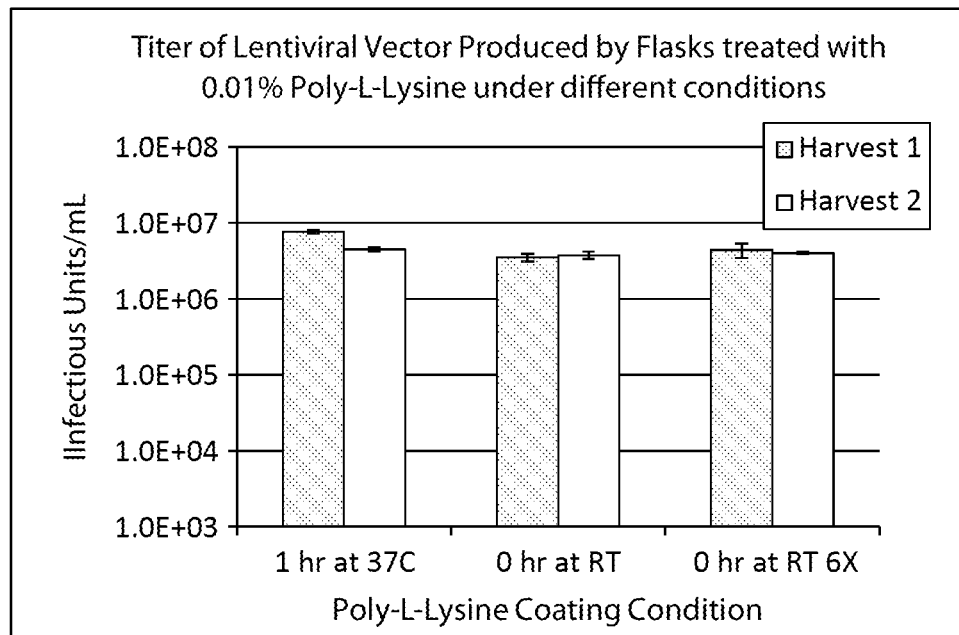
FIG. 7 depicts an experimentation examining impact of treating transfection vessels with poly-L-Lysine on viral production. Normalized viral titers and infection units for each flask treated with 0.01% poly-L-Lysine and harvest of transfected cells are plotted in (A) and (B).

Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* $3^{rd}$ ed., Cold Spring Harbor Laboratory Press (Cold Spring Harbor, N.Y. 2001), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the term "293F" is a designation of a cell line.

As used herein, the term "293T" is a designation of a cell line.

As used herein, the term "3T3" is a designation of a cell line.

As used herein, the term "cDNA" is an abbreviation of complimentary DNA.

As used herein, the term "cGMP" as it relates to virus production is an abbreviation of current good manufacturing practice.

As used herein, the term "D10" is an abbreviation of DMEM medium containing 10% of fetal bovine serum.

As used herein, the term "DMEM" is an abbreviation of a tissue culture medium, Dulbecco's Modified Eagles Medium.

As used herein, the term "DNA" is an abbreviation of Deoxyribonucleic Acid.

As used herein, the term "Eco" is an abbreviation of the Ecotropic envelope protein.

As used herein, the term "Env" is an abbreviation of an envelope protein.

As used herein, the term "FBS" is an abbreviation of fetal bovine serum.

As used herein, the term "GALV" is an abbreviation of the Gibbon Ape Leukemia Virus envelope.

As used herein, the term "GFP" is an abbreviation of green fluorescent protein.

As used herein, the term "HbF" is an abbreviation of fetal hemoglobin.

As used herein, the term "HEK293" is a designation of a cell line.

As used herein, the term "HIV" is an abbreviation of human immunodeficiency virus.

As used herein, the term "HT1080" is a designation of a cell line.

As used herein, the term "LCR" is an abbreviation of locus control region.

As used herein, the term "LTR" is an abbreviation of long terminal repeat.

As used herein, the term "LRF" is an abbreviation of Leukocyte Reduction Filter.

As used herein, the term "MCB" is an abbreviation of Master Cell Bank.

As used herein, the term "MEL Cells" is an abbreviation of murine erythroleukemia cells.

As used herein, the term "MIEG3" is a designation of a gamma-retroviral vector.

As used herein, the term "MPR" is an abbreviation of mannose 6-phosphate receptor.

As used herein, the term "NIH" is an abbreviation of National Institutes of Health.

As used herein, the term "NTP" is an abbreviation of national toxicology program.

As used herein, the term "PBS" is an abbreviation of Phosphate-Buffered Saline.

As used herein, the term "pCDNA3.MLV.g/p" is a designation of a plasmid containing packaging sequences.

As used herein, the term "PES" is an abbreviation of polyethersulfone.

As used herein, the term "PS" is an abbreviation of polysulfone.

As used herein, the term "RD114" is an abbreviation of the feline leukemia virus envelope.

As used herein, the term "SERS11.EGFP.pre*" is a designation of a gamma-retroviral vector.

As used herein, the term "SIN" is an abbreviation of self-inactivating.

As used herein, the term "SIN11.SF.eGFP.pre*" is a designation of a gamma-retroviral vector.

As used herein, the term "SRS11.EFS.IL2RGpre*" is a designation of a gamma-retroviral vector.

As used herein, the term "SRS11.SF.DsRed2.pre*" is a designation of a gamma-retroviral vector.

As used herein, the term "SRS11.SF.GFP.pre*SE" is a designation of a gamma-retroviral vector.

As used herein, the term "T225" is an abbreviation of a 225 cm$^2$ tissue culture flask.

As used herein, the term "T75" is an abbreviation of a 75 cm$^2$ tissue culture flask.

As used herein, the term "TFF" is an abbreviation of tangential-flow filtration.

Improved Vector Production

As disclosed herein, the need for clinical grade gamma-retroviral vectors with self-inactivating (SIN) long terminal repeats has prompted a shift in the method with which large scale c-grade vectors are produced, from the use of stable producer lines to transient transfection-based techniques. A method was developed based on the WAVE BIOREACTOR™ (rocking bioreactor with pre-sterile, disposable chamber) (GE Healthcare) production platform. This platform allows for large-scale closed-system production of high-titer retroviral vectors for clinical trials using transient transfection up to 25 Liters per harvest using closed system processing. The present patent application describes the development and scale-up procedures and reports on the successful use of the WAVE BIOREACTOR™ (rocking bioreactor with pre-sterile, disposable chamber) in the production of six cGMP grade retroviral vectors in support of the FDA's National Toxicology Program (NTP).

As further disclosed herein, in order to determine the optimal time of transfection, 293T cells were seeded onto FIBRA-CEL® (solid support cell growth matrix) and exposed to transfection reagents and plasmid DNA within hours of seeding as compared to cells that were transfected the following day. The data show a titer of less than $10^4$ IU/mL from cells that were transfected one day post-seeding as compared to cells that were transfected the same day. It has now been determined that optimal titers are achieved when cells are mixed with transfection reagents and plasmid DNA at the time of seeding onto FIBRA-CEL® (solid support cell growth matrix). Cells were plated at different cell densities, harvested and tested for virus production in five separate experiments using GALV pseudotyped gamma-retroviral vectors. Although the same number of cells was used for each group, titers varied greatly based on the plating density and were higher when cells were harvested from plates that had been seeded with a higher cell density. For scale-up, several parameters were tested including the time of media change post-transfection and the length of time the cells were exposed to PBS and TRYPLE™ SELECT (animal origin-free recombinant cell-dissociation enzyme) prior to transfection. To establish the amount of plasmid DNA necessary to improve titer, 293T cells were transfected side-by-side on tissue culture plastic as well as FIBRA-CEL® (solid support cell growth matrix). Where increasing plasmid DNA in static cultures produced a lower titer, increasing the DNA concentration on FIBRA-CEL® (solid support cell growth matrix) increased titer.

In one embodiment, the present invention provides a method of improving viral titer in a transfection-based production system using eukaryotic cells. In another embodiment, the cells harvested prior to transfection have progressed beyond log phase of cell growth. In another embodiment, the cells have achieved a state of confluency for at least 24 hours. In another embodiment, the cells are seeded at a cell density of at least $5 \times 10^4$ 4 to 5 days prior to cell harvest and transfection. In another embodiment, the cells are mixed with transfection reagents and plasmid DNA at the time of re-seeding into a new culture vessel. In another embodiment, the plasmid concentration used for transfection is at least 7 µg/ml of plasmid DNA. In another embodiment, the plasmid concentration used for transfection is at least 9.2 µg/ml of plasmid DNA. In another embodiment, the media is changed 12-24 hours post-transfection. In another embodiment, the media is changed 14-20 hours post-transfection. In another embodiment, the media is changed 19 hours post-transfection. In another embodiment, cells are rinsed with PBS followed by 3-8 minute exposure to TRYPLE™ SELECT (animal origin-free recombinant cell-dissociation enzyme) prior to transfection. In another embodiment, cells are rinsed with PBS followed by 4-7 minute exposure to TRYPLE™ SELECT (animal origin-free recombinant cell-dissociation enzyme) prior to transfection. In another embodiment, cells are rinsed with PBS followed by 5 minute exposure to TRYPLE™ SELECT (animal origin-free recombinant cell-dissociation enzyme) prior to transfection. In another embodiment, the harvesting, mixing, re-seeding, and/or transfection steps, alone or in combination, results in improved viral titer compared to traditional protocols of transfection-based production using eukaryotic cells. In another embodiment, the cells are 293T cells. In another embodiment, the vector is a SIN lentiviral vector. In another embodiment, the vector is an LTR-driven Gamma-Retroviral vector. In another embodiment, the vector is a SIN Gamma-retroviral vector. In another embodiment, the gamma-retroviral or lentiviral vectors produced are cGMP grade vectors. In another embodiment, the vectors are produced in a closed system bioreactor.

As further disclosed herein, treatment of tissue culture vessel with 0.01% of poly-L-lysine, performed prior to the addition of mammalian cells and calcium phosphate-based transfection reagents, leads to higher viral titer due to reducing cell loss post-transfection (Example 11, FIG. 7). Tissue culture vessel treated up to 72 hours prior to use, either stored containing 0.01% of poly-L-lysine or after removal of poly-L-lysine, give rise to equal viral titers when used for calcium-phosphate transfection of mammalian cells (Example 12, FIG. 8).

Accordingly, in one embodiment, a method of improving viral titer in a transfection-based production system using eukaryotic cells is provided. In some embodiments, the method comprises treating tissue culture vessel with poly-L-lysine prior to addition of mammalian cells and calcium phosphate-based transfection reagents. Particularly, in some embodiments, the treatment is performed by storing poly-L-lysine solution in the tissue culture vessel before use. In other embodiments, the treatment is performed by rinsing the tissue culture vessel with poly-L-lysine solution and subsequently removing the solution before use. In some embodiments, the method comprising treating tissue culture vessel with 0.01% poly-L-lysine solution. In some embodiments, the method comprises treating the tissue culture vessel 0 to 72 hours prior to use.

As further disclosed herein, lentiviral vector is generated in mammalian cells after transfection of the cells with the vector and 3 different plasmids, which are the Gag/Pol plasmid, the Rev gene plasmid, and the envelope gene plasmid. Although the Gag/Pol plasmid includes the Rev gene, adding Rev gene plasmid in the transfection mixture increases the titer of lentiviral vector produced using calcium-phosphate transfection (Example 13, FIGS. 9A and 9B).

Accordingly, in one embodiment, a method of improving viral titer in a transfection-based production system using eukaryotic cells is provided. In some embodiments, the method comprises transfecting cells with a lentiviral vector and one or more plasmids containing the viral Gag/Pol gene, the Rev gene and/or the Envelop gene. In some embodiments, the method comprises increasing content of a plasmid containing viral Rev gene in a transfection mixture. In some embodiments, the method comprises transfecting cells with a transfection mixture contacting 1, 2, 3, 4 or 5 mole equivalents of Rev gene plasmid. In some embodiments, the method comprises transfecting $2 \times 10^7$ cells with 18 ml transfection mixture containing 18 µg lentiviral vector, 11.3 µg Gag/Pol plasmid, 3 µg Envelop gene plasmid and 0 to 10 µg Rev gene plasmid.

Figure 10:
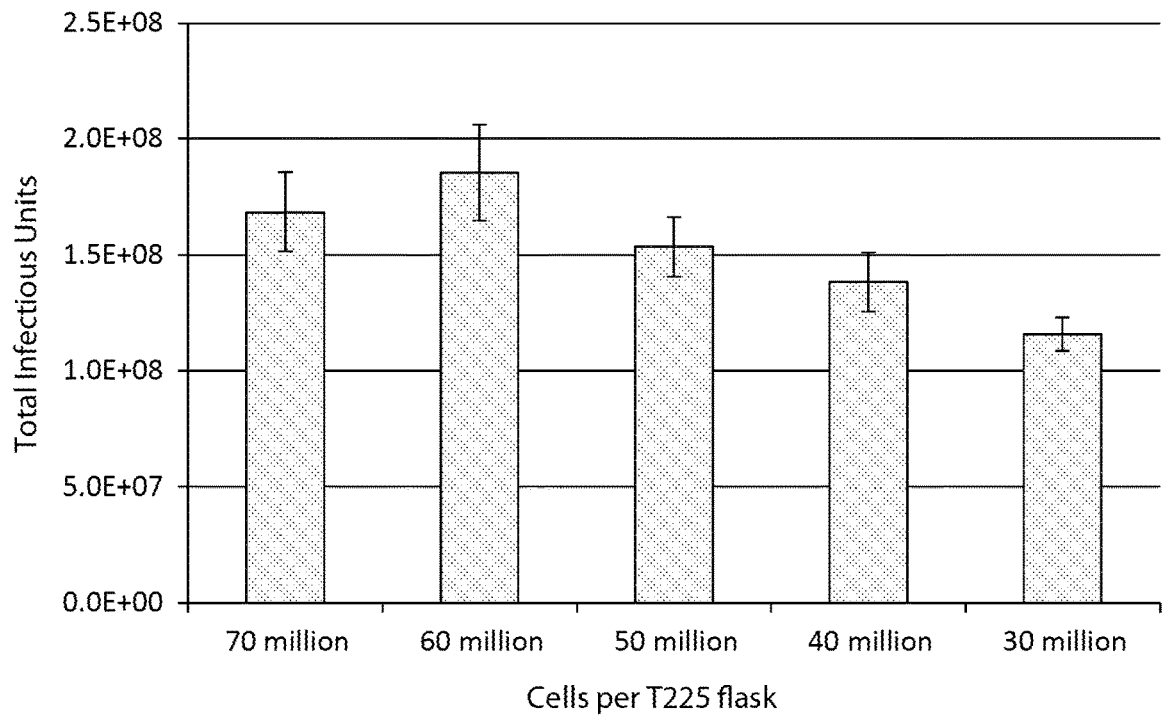
FIG. 10 depicts an experimentation examining the impact of transfection cell density on viral production. Total normalized infectious units of lentiviral vector per flask plated at 30-70 million cells per flask are plotted (mean and standard deviation).

As further disclosed herein, plating density of 60 million transfected 293T cells per T225 flask, or approximately $2.5 \times 10^5$ cells per square centimeter is optimal for virus production (Example 14, FIG. 10).

Accordingly, in one embodiment, a method of improving viral titer in a transfection-based production system using eukaryotic cells is provided. In some embodiments, the method comprises plating cells at a density of about 60 million cells per T225 flask. In other embodiments, the method comprises plating cells at a density of about $2.5 \times 10^5$ cells per square centimeter.

Figure 11A:
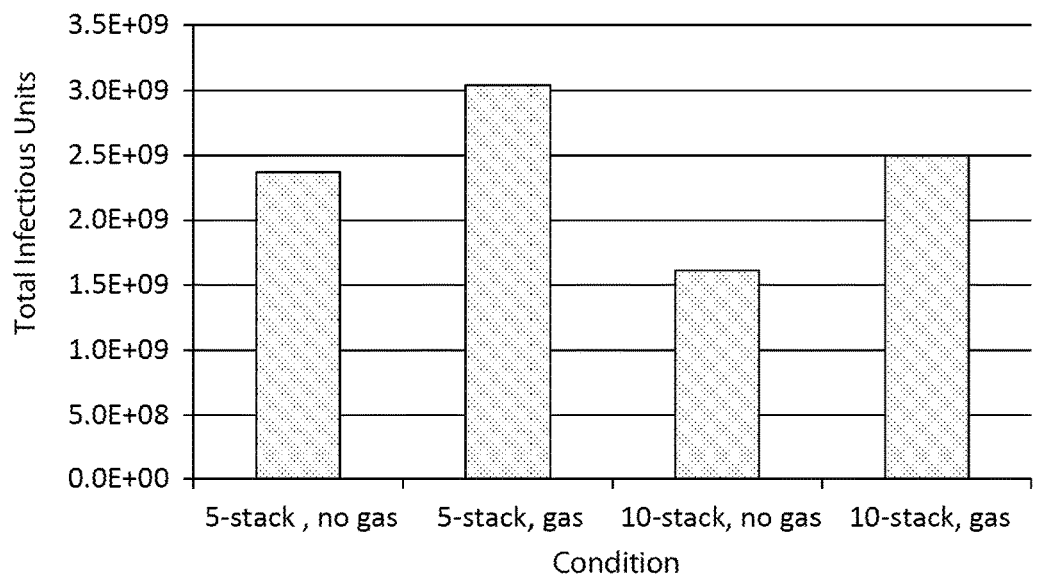
FIG. 11 depicts an experimentation examining the impact of transfection vessels and $CO_2$ treatment of transfection vessels on viral production. Total infectious units of virus produced by each 5- or 10-layer CELLSTACK™ (stacked culture vessel) with/without flushing with gas are summarized in (A); total infectious units of virus produced per square centimeter of 5- or 10-layer CELLSTACK™ (stacked culture vessel) with/without flushing with gas are plotted in (B).
Figure 11B:
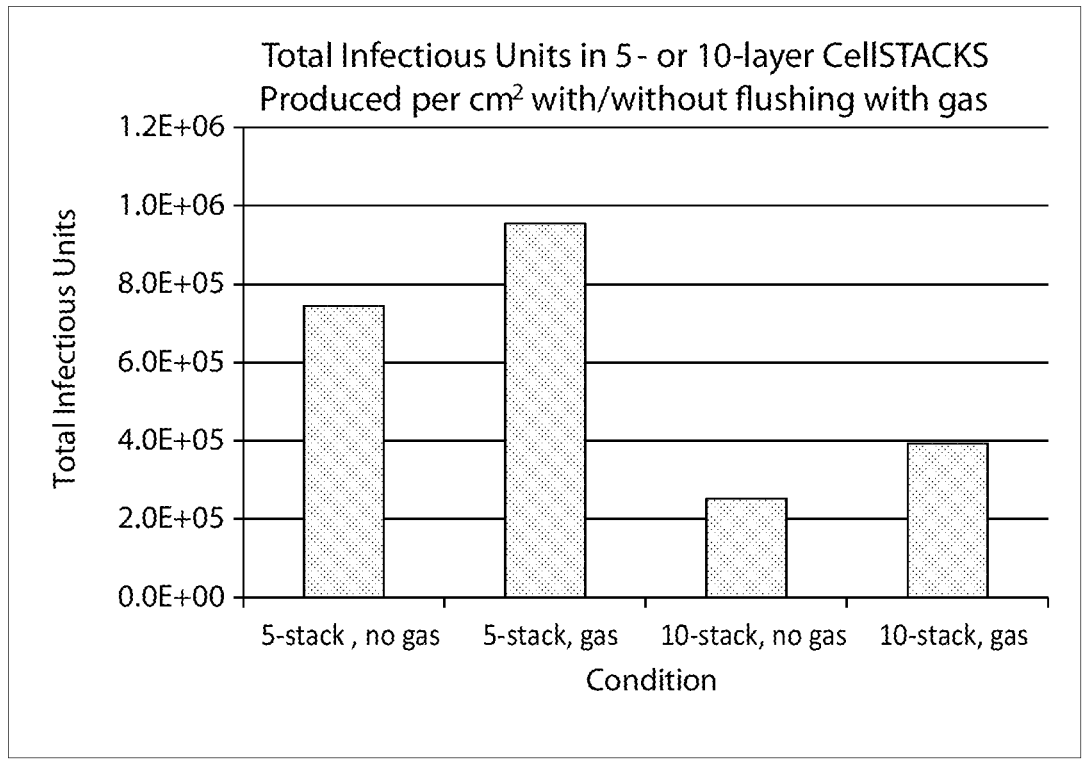

As further disclosed herein, mammalian cells transfected in CORNING® 5-layer CELLSTACK™ (stacked culture vessel) generate higher titer of lentiviral vector as opposed to cells transfected in 10-layer CELLSTACK™ (stacked culture vessel) (Example 15, FIG. 11B).

Accordingly, in one embodiment, a method of improving viral titer in a transfection-based production system using eukaryotic cells is provided. In some embodiments, the method comprises transfecting cells in a CORNING® 5-layer CELLSTACK™ (stacked culture vessel).

As further disclosed herein, after each post-transfection manipulation, gassing of each CELLSTACK™ (stacked culture vessel) and Tissue Culture Flask for 30 seconds with 5% $CO_2$/40% $O_2$ prior to placing the CELLSTACK™ (stacked culture vessel) into the incubator improves viral vector titer (Example 15, FIG. 11B; Example 16, FIG. 12; and Example 17, FIG. 13).

Accordingly, in one embodiment, a method of improving viral titer in a transfection-based production system using eukaryotic cells is provided. In some embodiments, the method comprises gassing a culture vessel containing transfected cells after transfection and prior to placing the culture vessel into an incubator. In some embodiments, the method comprises gassing a culture vessel with $CO_2$. Particularly, in some embodiments, the method comprises gassing a tissue culture vessel with 5% $CO_2$. In some embodiments, the method comprises gassing a culture vessel with a mixture of $O_2$ and $CO_2$. Particularly, in some embodiments, the method comprises gassing a tissue culture vessel with 5% $CO_2$/40% $O_2$. In some embodiments, the method comprises gassing the tissue culture vessel for 30 seconds.

Figures 14A, 14B:
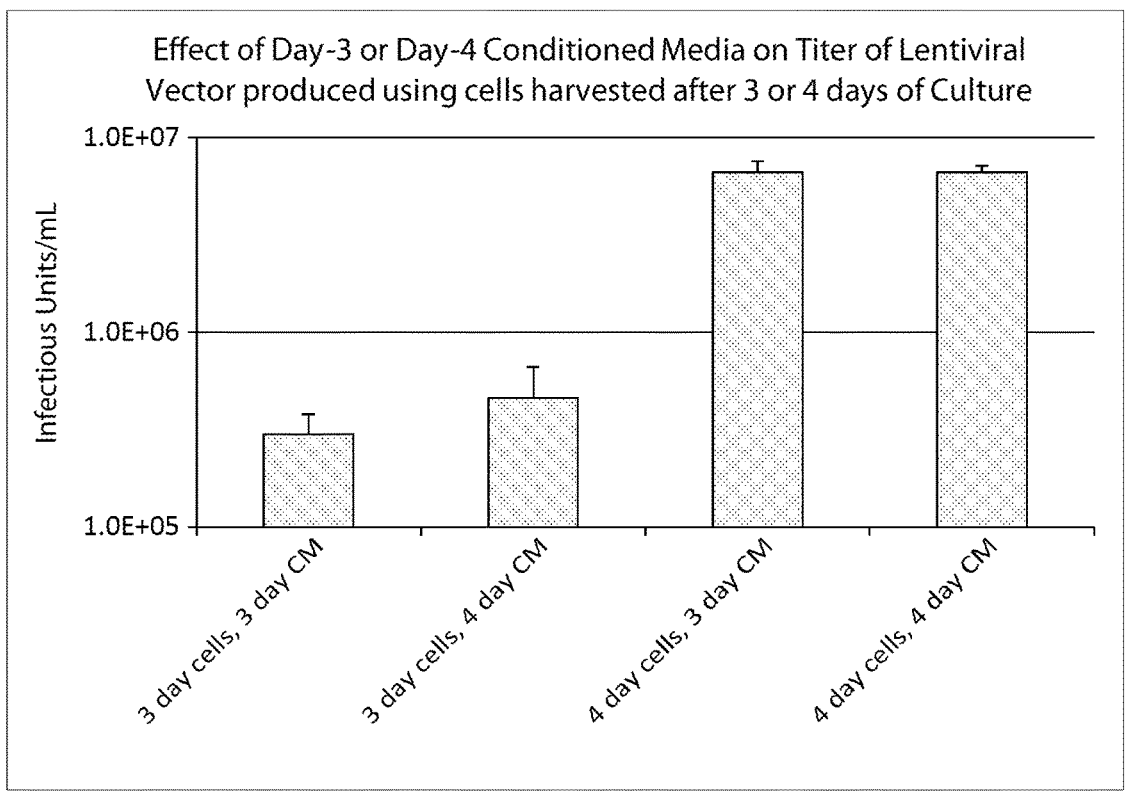
FIG. 14 depicts an experimentation examining the optimal combination of times for pre-transfection cell seeding and time interval for preparing conditioned media. Transfection conditions of different timelines are shown in (A); infectious units of virus for each condition are plotted in (B), which shows the effect of day-3 or day-4 conditioned media on titer of lentiviral vector produced using cells harvested after 3 or 4 days of culture.
Figure 22:
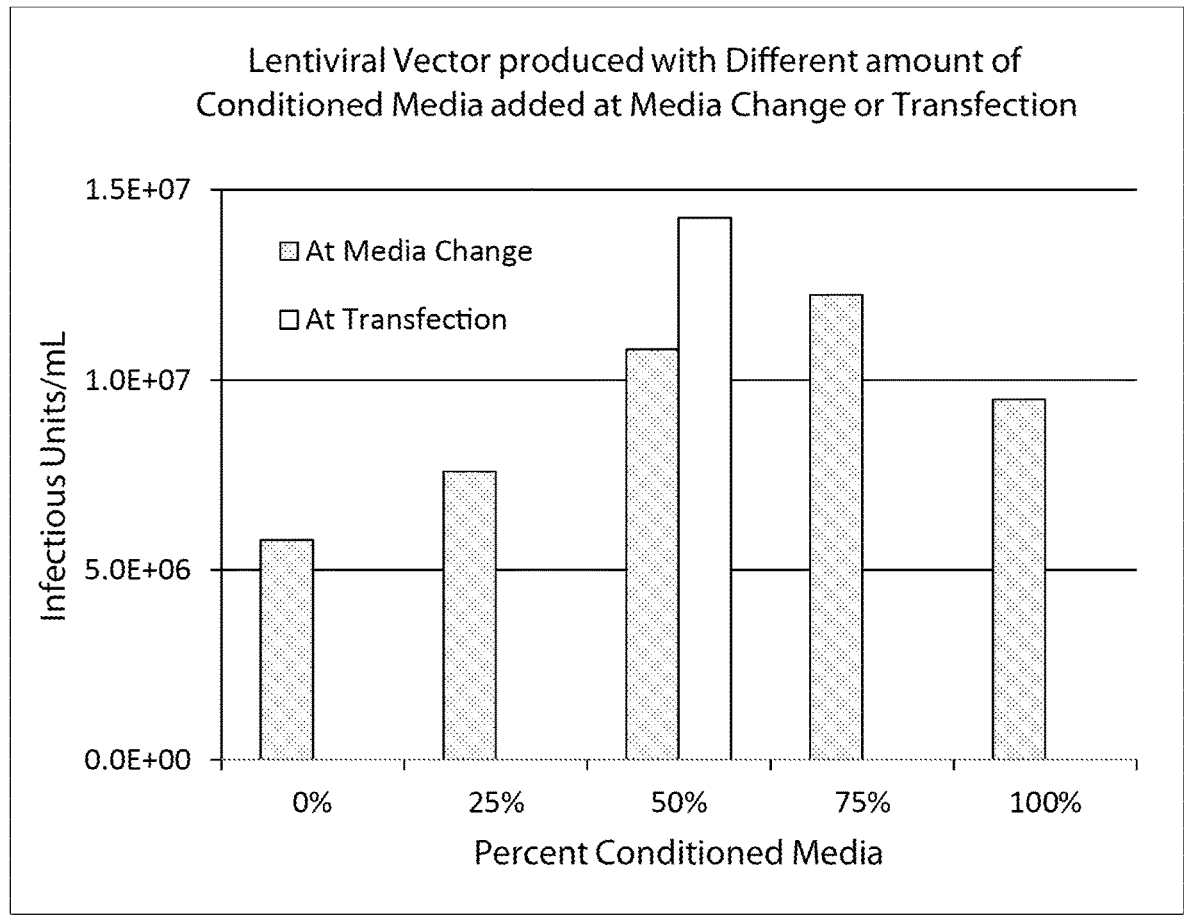
FIG. 22 depicts an experimentation demonstrating that addition of at least 50% conditioned-media, set aside from the cell harvest the day of transfection, increases vector titer when added at the time of transfection or at media change.

As further disclosed herein, the use of at least 50% conditioned media at the media change, set aside from the cell harvest the day of transfection, increases vector titer (FIG. 22). Cells cultured for 4 days with conditioned media are superior as compared to cells cultured for 3 days (FIG. 14B, Example 18).

Accordingly, in one embodiment, a method of improving viral titer in a transfection-based production system using eukaryotic cells is provided. In some embodiments, the method comprises culturing transfected cells in conditioned culture media. In some embodiments, the method comprises re-feeding transfected cells with conditioned culture media during culture media change after transfection. In some embodiments, the conditioned media is collected from cell harvest before transfection. In some embodiments, the conditioned culture media is a media in which cells have grown for 3 or 4 days before harvested for transfection.

Figure 15:
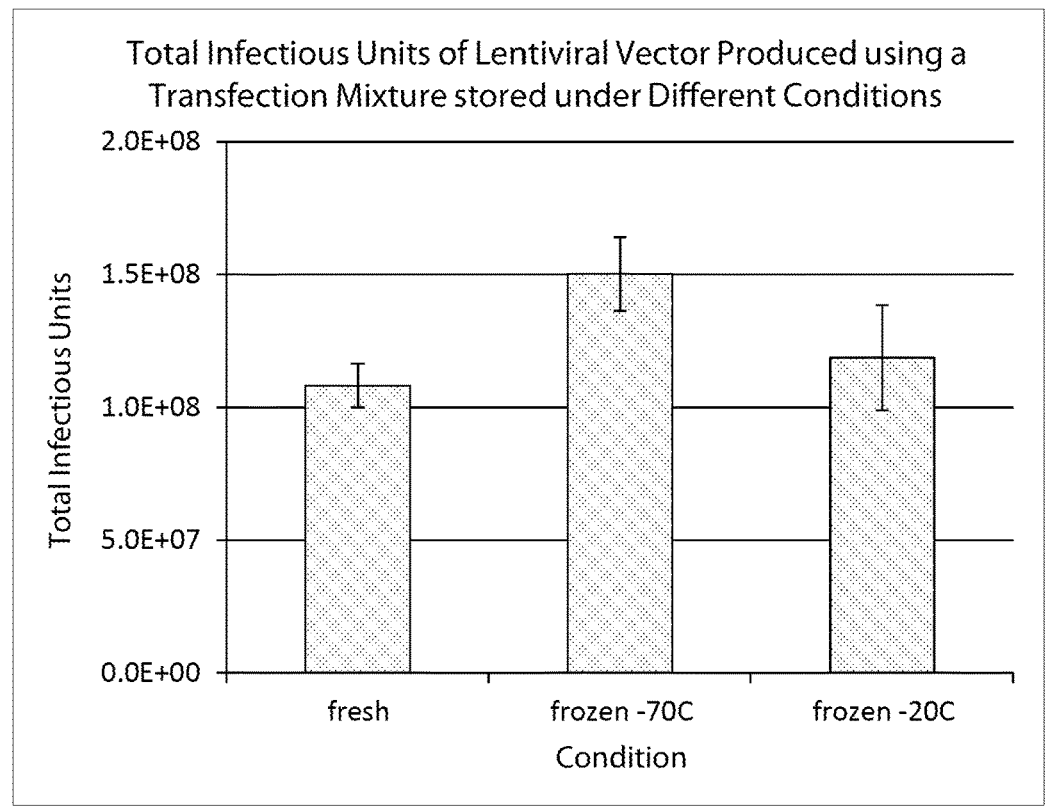
FIG. 15 depicts an experimentation comparing effects of fresh and frozen transfection mixtures on lentiviral vector production. Total infectious units produced by transfection mixtures stored fresh or frozen transfection mixtures are plotted (triplicate groups).
Figure 16:
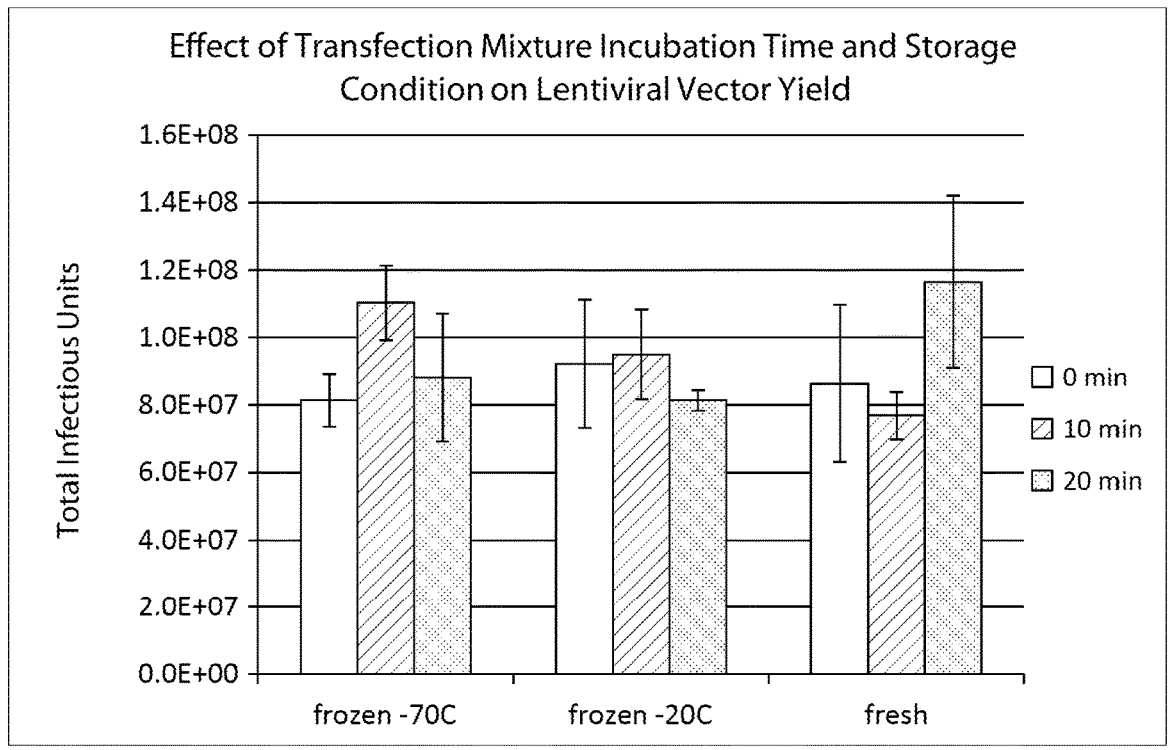
FIG. 16 depicts an experimentation comparing the effect of pre-made transfection mixture stored at −20 C and at −70 C on viral production, thereby showing the effect of time and storage conditions. This experimentation also compares the impact of 0-, 10- and 20-minute incubations with transfection mixture on viral production. Average yields from each group are plotted (triplicate groups).
Figure 17:
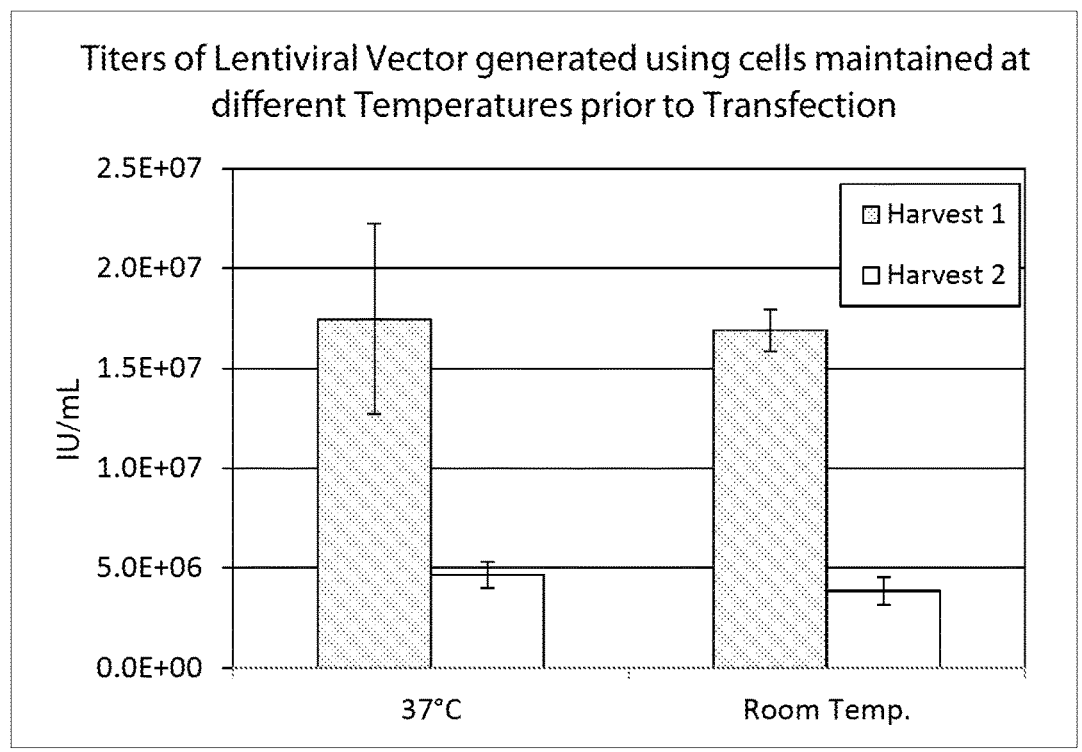
FIG. 17 depicts an experimentation examining the impact on viral production of incubating cell suspensions at 37 C compared to room (ambient) temperature before introducing the transfection mixture, thereby showing the effect of maintaining cells at different temperatures prior to transfection. Average titers per harvest of supernatant from cell suspensions incubated at each temperature are plotted (triplicate groups).
Figure 18:
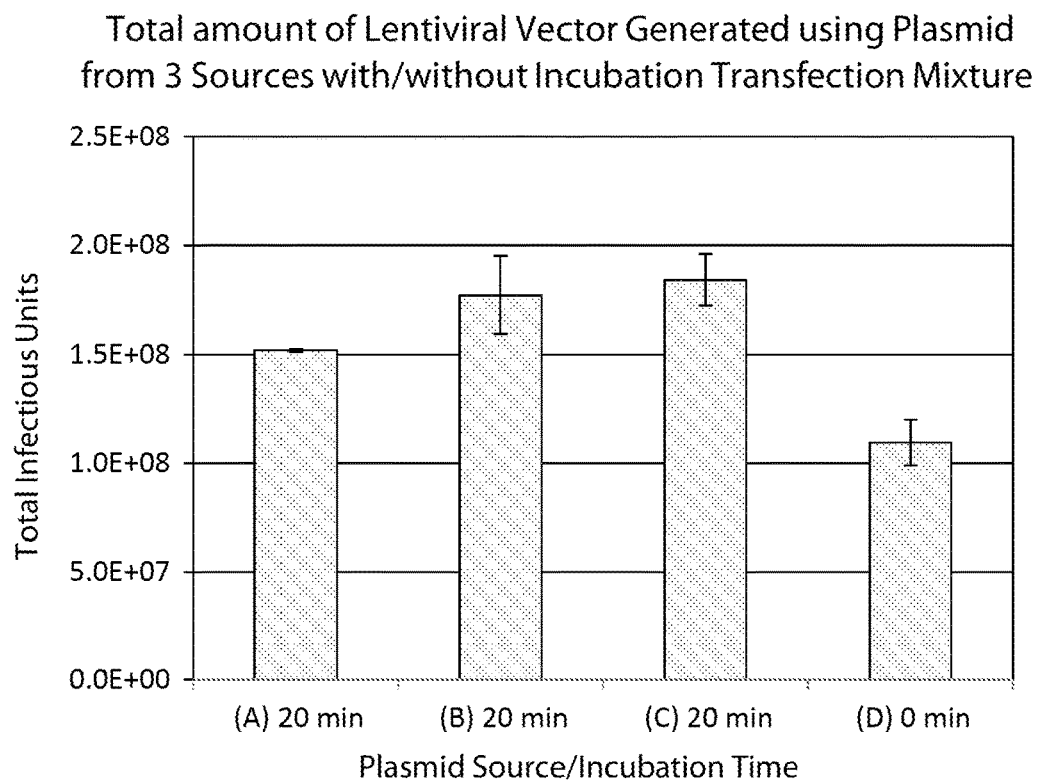
FIG. 18 depicts an experimentation comparing lentiviral vector titers of supernatant produced with different sources of plasmids. This experimentation also examines the effect of a 20-minute incubation of transfection mixtures. Total infectious units of virus produced by each group are plotted (triplicate groups).

As further disclosed herein, a calcium phosphate transfection mixture that has been diluted 4-fold with media containing fetal bovine serum, or alternate protein source, can be stored frozen at −20° C. or −80° C. without losing the ability to effectively transduce cells upon thawing as compared to transfection mixture prepared immediately prior to use (Example 19, FIG. 15; Example 20, FIG. 16). Cells diluted with media may be prepared and stored at ambient temperature prior to use without lower titer as compared to cells maintained at 37° C. (Example 21; FIG. 17). Transfection mixture incubated for 20 minutes as opposed to 0 minutes prior to addition to the cells leads to higher vector titer (Example 22; FIG. 18).

Accordingly, in one embodiment, a method of improving viral titer in a transfection-based production system using eukaryotic cells is provided. In some embodiments, the method comprises incubating a transfection mixture before addition to cells. Particularly, in some embodiments, the method comprises incubating a transfection mixture for 20 minutes at ambient temperature before addition to cells As further disclosed herein, lentiviral vector can be efficiently captured from cell-free serum-containing or serum-free cell supernatant harvested at 48 and 72 hours after calcium-phosphate transfection using a MUSTANG® Q anion-exchange capsule, where the capsule is sanitized using 1 Molar NaOH, pre-conditioned using 1 Molar NaCl, and equilibrated using 25 mMolar Tris-HCl (pH 8.0), 150 mMolar NaCl prior to viral capture. The MUSTANG® Q anion-exchange capsule used to capture lentiviral vector from cell-free cell supernatant can be rinsed with 25 mMolar Tris-HCl (pH 8.0), 150 mMolar NaCl after viral capture without elution of the viral vector. Lentiviral vector bound to a MUSTANG® Q anion-exchange capsule can be efficiently eluted from the capsule using 25 mMolar Tris-HCl (pH 8.0), 1.2 M NaCl. A 3-fold dilution with 25 mMolar Tris-HCl (pH 8.0) within 2 minutes of the start of collection of eluted virus minimizes loss of viral titer. Data show that exposure to 300 mMolar NaCl does reduce vector titer, but that loss is reduced when exposure is shortened (Example 23 FIG. 19).

Accordingly, in one embodiment, a method of improving viral titer in a transfection-based production system using eukaryotic cells is provided. In some embodiments, the method comprises capturing viral vectors from cell-free supernatant using an anion-exchange capsule. In some embodiments, the anion-exchange capsule can be sanitized using NaOH, pre-conditioned using NaCl, and equilibrated using Tris-HCl (pH 8.0) and NaCl prior to viral capture. Particularly, in some embodiments, the anion-exchange capsule can be sanitized using 1 Molar NaOH. In some embodiments, the anion-exchange capsule can be pre-conditioned using1 Molar NaCl. In some embodiments, the anion-exchange capsule can be equilibrated using 25 mMolar Tris-HCl (pH 8.0), and 150 mMolar NaCl. In some embodiments, the anion-exchange capsule can be rinsed with Tris-HCl (pH 8.0) and NaCl after viral capture. Particularly, in some embodiments, the anion-exchange capsule can be rinsed with 25 mMolar Tris-HCl (pH 8.0), and 150 mMolar NaCl. In some embodiments, captured viral vector can be eluted from the anion-exchange capsule using Tris-HCl (pH 8.0), and NaCl. Particularly, in some embodiments, captured viral vector can be eluted from the anion-exchange capsule using 25 mMolar Tris-HCl (pH 8.0), 1.2 M NaCl. In some embodiment, the anion-exchange capsule is a MUSTANG® Q anion-exchange capsule. In some embodiment, the viral vector is a lentiviral vector.

Figure 20:
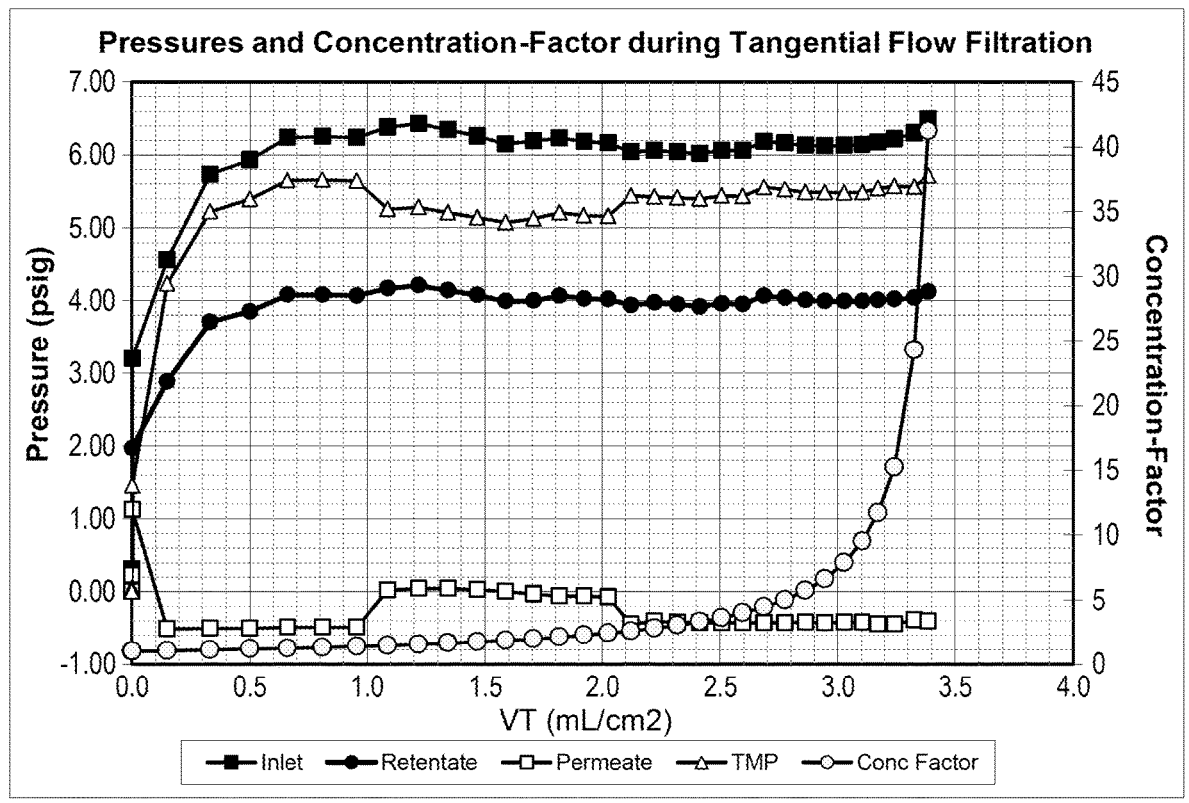
FIG. 20 depicts efficient concentration of up to 40-fold of lentiviral vector collected from a MUSTANG® Q anion-exchange capsule in 25 mMolar Tris-HCl (pH 8.0), 400 mMolar NaCl with tangential-flow filtration (TFF) using a 500 kDa Polysulfone (PS) TFF module using a transmembrane pressure of 5-6 psi and shear of 5000 to 6000 $s^{-1}$.

As further disclosed herein, lentiviral vector collected from a MUSTANG® Q anion-exchange capsule in 25 mMolar Tris-HCl (pH 8.0), 400 mMolar NaCl can be efficiently concentrated up to 40-fold with tangential-flow filtration (TFF) using a 500 kDa Polysulfone (PS) TFF module using a trans-membrane pressure of 5-6 psi and shear of 5000 to 6000 s$^{-1}$. (FIG. 20). A higher number of particles can be recovered when air is introduced into the TFF loop prior to harvest of the concentrated product from the module (Example 24, FIG. 21B).

Accordingly, in one embodiment, a method of improving viral titer in a transfection-based production system using eukaryotic cells is provided. In some embodiments, the method comprises concentrating viral vector recovered from an anion-exchange capsule using a tangential-flow filtration (TFF) module. In some embodiments, the TFF module is a Polysulfone (PS) module. In other embodiments, the TFF module is a polyether (PES) module. In some embodiments, the method comprises applying a trans-membrane pressure of 5-6 psi and shear of 5000 to 6000 s$^{-1}$ during tangential-flow filtration. In some embodiments, the method comprises introducing air into the TFF loop prior to harvest of concentrated product from the TFF module.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Optimizing Closed-System Production of High-Titer Retroviral Vectors

The need for clinical grade gamma-retroviral vectors with self-inactivating (SIN) long terminal repeats has prompted a shift in the method with which large scale cGMP-grade vectors are produced, from the use of stable producer lines to transient transfection-based techniques. The Vector Production Facility, an academic cGMP manufacturing laboratory that is part of the Translational Core Laboratories at the Cincinnati Children's Research Foundation, has developed such a method based on the WAVE BIOREACTOR™ (rocking bioreactor with pre-sterile, disposable chamber) (GE Healthcare) production platform. This platform allows for large scale closed-system production of high-titer retroviral vectors for clinical trials using transient transfection up to 25 Liters per harvest using closed system processing.

The present application describes the development and scale-up procedures and reports on the successful use of the WAVE BIOREACTOR™ (rocking bioreactor with pre-sterile, disposable chamber) in the production of six cGMP grade retroviral vectors in support of the FDA's National Toxicology Program (NTP).

Example 2

Transfection

Adherent 293T cells were transfected in T75 or T225 flasks or on 2 gram of FIBRA-CEL® (solid support cell growth matrix) discs in ridged 850 cm² roller bottles (10 mL/T75; 30 mL/T225; 100 mL/roller bottle). Non-adherent 293F cells were grown in suspension culture and transfected in either serum-free FREESTYLE™ 293 (animal origin free, chemically defined, protein free) media (non-adherent conditions), or in FREESTYLE™ 293 (animal origin free, chemically defined, protein free) media or DMEM supplemented with FBS (adherent conditions) in tissue culture flasks. Transfections were done using Calcium Phosphate (adherent conditions only), LIPOFECTAMINE™ 2000 (transfection reagent), or FECTURIN™ (transfection reagent) according to the manufacturer's instructions. Vector was collected at 12 or 24 hour intervals, filtered at 0.45 µm, and frozen at or below −70° C. In the Bioreactor (suspension cells or adherent cells on FIBRA-CEL® (solid support cell growth matrix)), higher titers were obtained when a higher concentration of plasmid was utilized (9.2 performed better than 6.9 or 4.6 microgram of total plasmid/mL media). Higher concentrations were not tested but may result in even further enhancements.

Example 3

Large Scale Virus Production

Cells from a certified 293T master cell bank (MCB) were expanded on tissue culture plastic, harvested, mixed with calcium phosphate transfection reagents and plasmid (4 g vector, 3.6 gram gag/pol, 1.6 gram env per Liter), and pumped into a WAVE CELLBAG™ (pre-sterilized, single use bioreactor chamber) (GE Healthcare) containing FIBRA-CEL® (solid support cell growth matrix) discs (New Brunswick) in DMEM with 10% FBS (D10). Cells were cultured at 37° C., 5% $CO_2$ using a rocking speed of 22 rpm and 6° angle. At 16-20 hours post-transfection, the media was exchanged; virus was harvested at approximately 12-hour intervals, filtered through a leukocyte reduction filter (Pall), aliquoted into CRYOCYTE™ freezing containers using a closed system fluid path, placed in protective freezing cassettes and frozen at or below −70° C.

Example 4

Titration

Vector pseudotyped with an ecotropic envelope was titered on NIH 3T3 cells, vector pseudotyped with the Gibbon Ape Leukemia (GALV) or Feline Leukemia Virus (RD114) envelope was titered on HT1080 cells. SIN lentivirus vector pseudotyped with the Vesicular Stomatitis Virus Glycoprotein (VSV-G) are titered on either HT1080 or, for vectors expressing the hemoglobin gene under the control of a globin-promoter, Murine Erythroleukemia (MEL) cells. Titers were calculated based on the % GFP expression or the % of cells positive for hemoglobin expression based on detection by a hemoglobin-specific antibody as determined by FACS, or based on copy number as determined by vector specific quantitative PCR.

Example 5

Suspension Culture

Initial pilot studies and scale-up were done with HEK293-derived 293F cells (Invitrogen) grown in serum-free (SF) FREESTYLE™ 293 (animal origin free, chemically defined, protein free) media (Invitrogen) as suspension cells are easier to manipulate in a bioreactor. Studies show up to 10-fold expansion over 5 days with cell viability at or above 80% (FIG. 1). However, 293F cells produced a 20-fold lower titer when transfected under adherent conditions in D10 with Ca-Phosphate (FIG. 2) and no detectable titer with other transfection reagents or under non-adherent conditions.

Example 6

Adherent Cell Culture

FIBRA-CEL® (solid support cell growth matrix) disks (New Brunswick Scientific) are available as a sterile pre-loaded substrate for the WAVE BIOREACTOR™ (rocking bioreactor with pre-sterile, disposable chamber) (at 20 gram per Liter) to support growth of adherent cells. Small scale pilot studies using adherent 293T cells were performed in 850 cm² ridged roller bottles with 2 gram FIBRA-CEL® (solid support cell growth matrix) discs per $2 \times 10^8$ 293T cells per 100 mL of D10. Post-seeding, cells migrate inside of the matrix and continue to expand as can be determined by glucose consumption over time. Glucose levels in a 1 Liter bioreactor that had been seeded with $2 \times 10^9$ transfected 293T cells showed that the media should be changed at approximately 12 hour intervals to maintain a glucose level above 100 mg/dL. Treatment with TRYPLE™ SELECT (animal origin-free recombinant cell-dissociation enzyme) for up to 30 minutes allows up to 20% of the post-production cells to be released and harvested while the majority of cells maintain trapped in the matrix.

Example 7

Time of Transfection

To determine the optimal time of transfection, 293T cells were seeded onto FIBRA-CEL® (solid support cell growth matrix) and exposed to transfection reagents and plasmid DNA within hours of seeding as compared to cells that were transfected the following day. The data show a titer of less than $10^4$ IU/mL from cells that were transfected one day post-seeding as compared to cells that were transfected the same day (FIG. 3). It has now been determined that optimal titers are achieved when cells are mixed with transfection reagents and plasmid DNA at the time of seeding onto FIBRA-CEL® (solid support cell growth matrix).

Example 8

Plasmid DNA

To establish the amount of plasmid DNA needed for optimal titer, 293T cells were transfected side-by-side on tissue culture plastic as well as on FIBRA-CEL® (solid support cell growth matrix). Where increasing plasmid DNA in static cultures produced a lower titer, increasing the DNA concentration on FIBRA-CEL® (solid support cell growth matrix) increased titer as shown in a representative dataset (FIG. 4) out of a total of 3 experiments.

Example 9

Cell Culture

Cells were plated at different cell densities (from $2.5 \times 10^4$ cells/cm² through $1 \times 10^5$ cells/cm²) 4 days prior to transfection, harvested and tested for virus production in five separate experiments using GALV pseudotyped gamma-retroviral vectors. Although the same number of cells was used for each group, titers on plastic surface as well as on FIBRA-CEL® (solid support cell growth matrix) cultures in the bioreactor varied greatly based on the plating density and were higher when cells were harvested from plates that had been seeded with a higher cell density (>$2.5 \times 10^4$ cells/cm$^2$) (FIG. 5).

Example 10

Scale-Up

Several parameters were tested including the time of media change post-transfection (FIG. 6A) and the length of time cells were exposed to PBS and TRYPLE™ SELECT (animal origin-free recombinant cell-dissociation enzyme) prior to transfection (FIG. 6B). For media change, 19 hours was found to be optimal in two separate experiments (representative experiment shown). Although all cells had >95% viability after exposure to PBS and TRYPLE™ SELECT (animal origin-free recombinant cell-dissociation enzyme), cells exposed for a shorter period of time generated higher titers.

Example 11

Poly-L-Lysine Timing

Figure 7B:
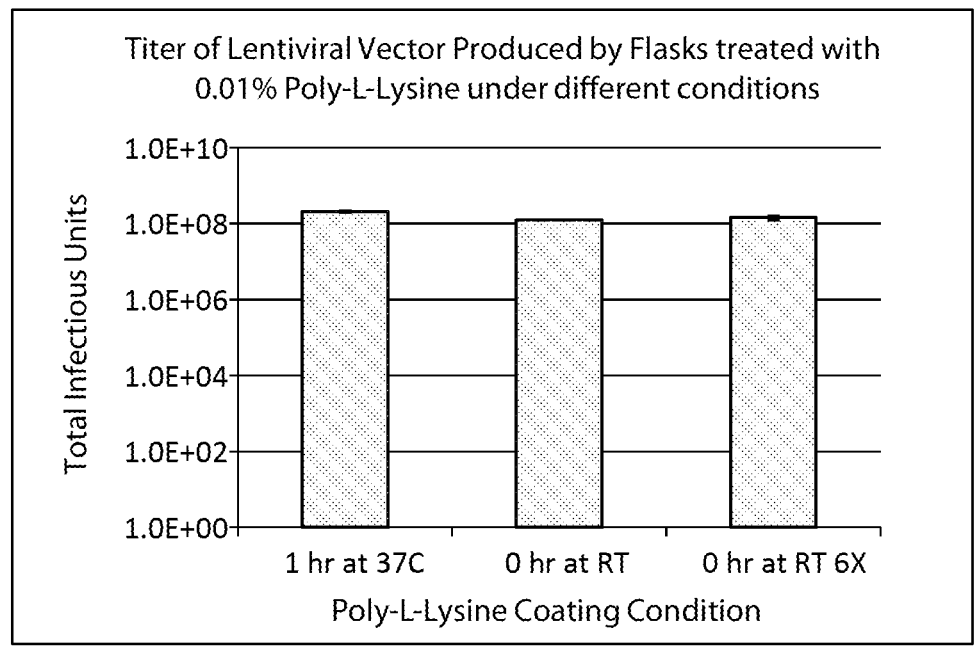
Figure 8A:
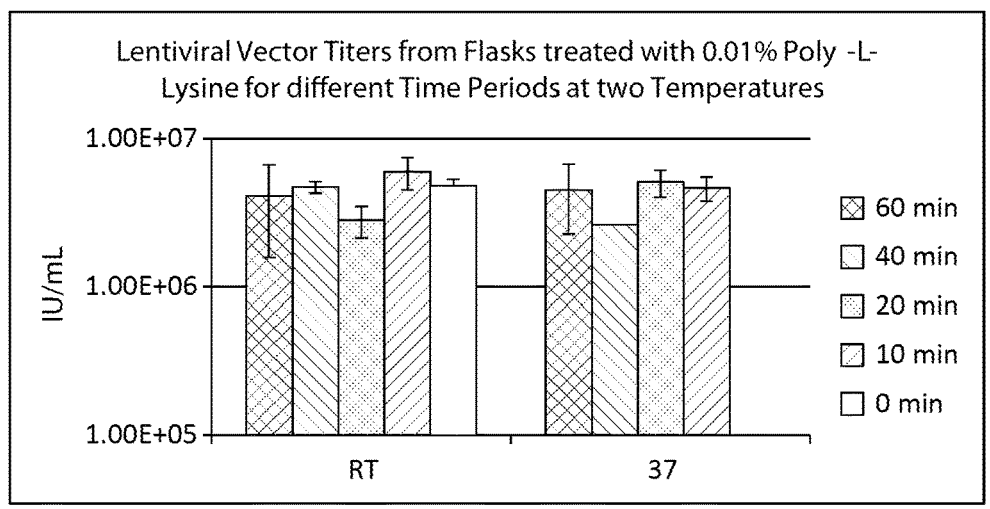
FIG. 8 depicts an experimentation examining the impact of pretreating transfection vessels with poly-L-Lysine on or 3 days before the transfection day on viral production. Lentiviral vector titers from flasks treated with 0.01% poly-L-Lysine for different temperatures and under different conditions are shown in (A) and (B); conditions of storage of poly-L-Lysine treated plates are shown in (C).
Figure 8B:
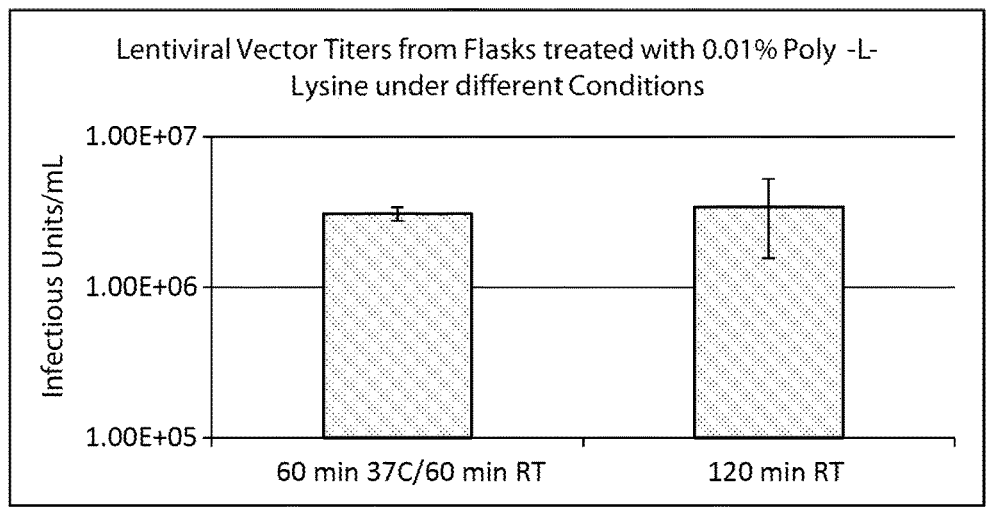

Experimentation has been performed to compare incubation conditions for poly-L-lysine (PLL). PLL was used at 0.01%, Sigma Cat. #P4832. The experimental conditions included:
Incubation at 1 hour, 37° C. (1 hr at 37° C.)
No incubation, flasks held at room temperature (RT)
PLL used after a total of six times (6×)
The experimental procedure is described below:
293T cells were seeded four days prior to transfection at $5 \times 10^4$ cells/cm$^2$. Three T75 flasks were treated with poly-L-lysine and incubated for one hour at 37° C., 5% CO$_2$ before removing poly-L-lysine. Three T75 flasks were treated with poly-L-lysine by applying, distributing, and then immediately removing the poly-L-lysine. These flasks were not incubated at 37° C., 5% CO$_2$ before transfection. The poly-L-lysine applied to two of the three T75 flasks was used to treat 6 more flasks in sequence. The sixth flask from each group was used for transfection. These flasks were also not incubated at 37° C., 5% CO$_2$ before transfection. 293T cells were harvested, and conditioned media was collected, 0.45 µm filtered, and stored at 4° C. 293T cells were transfected and seeded in D10. After approximately 16-19 hours of incubation at 37° C., 5% CO$_2$, cells were re-fed with at least 50% conditioned media, 50% fresh D10. Approximately 16 hours before Harvest 1, each flask was treated with 10 mMolar MgCl$_2$ and 50 Units/mL benzonase. Approximately 24 hours after media change, supernatant was harvested from each flask, 0.45 µm filtered, and aliquots were prepared for testing and frozen at −80° C. Flasks were re-fed. Approximately 24 hours after Harvest 1, a second harvest was performed and sampled. Flasks were discarded. Infectious titer was measured on MEL cells. The experimental results are shown in FIG. 7A and FIG. 7B.

The data from this experimentation suggests that a 1 hour, 37° C. incubation of the PLL coated plates may be beneficial.

Example 12

Plastic Integrity with Poly-L-Lysine

Experimentation has been performed to investigate if flasks can be pre-treated with Poly-L-Lysine days before transfection, in order to save time on Transfection Day during a large Lentivirus production.

Figure 8C:
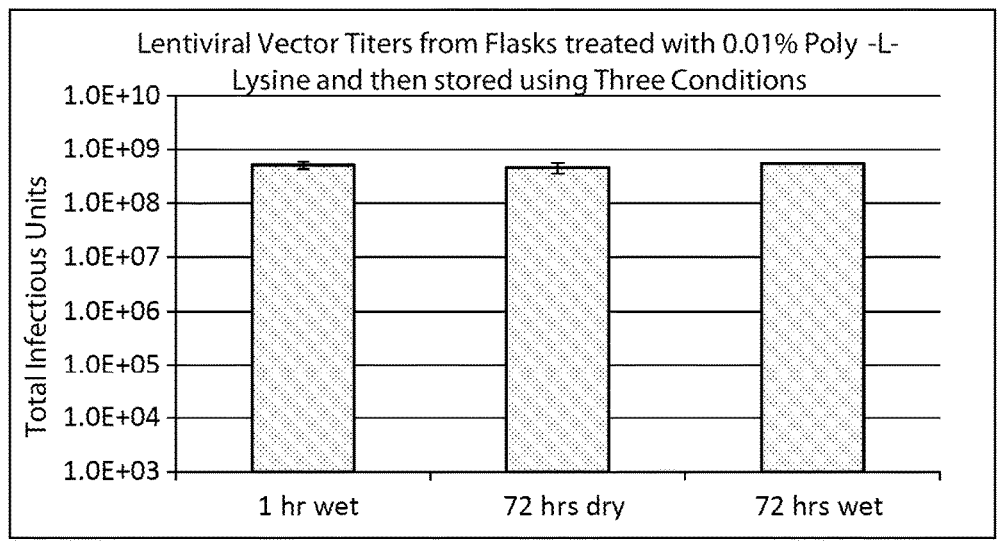

The experimental procedure is described below:
Seed 293T cells at $5 \times 10^4$ cells/cm$^2$ four days prior to transfection. Three days prior to transfection, treat four T-225 flasks with 0.01% PLL. Incubate at 37 C for 1 hour. Remove flasks from incubator and store at indicated conditions. Approximately 16 hours before the first harvest, treat flasks with 50 Units/mL benzonase and 10 mMolar MgCl$_2$. Approximately 24 hours after media change, collect Harvest 1 and 0.45 µm filter supernatant. Re-feed flasks 100% fresh warm D10, and continue incubation. Collect Harvest 2 after another 24 hours. Freeze aliquots of Harvests 1 and 2 for testing. Measure infectious titer on MEL cells. The results are shown in FIG. 8C. Additional testing includes treatment of flasks with 0.01% PLL at Room Temperature (RT) or 37 C for 0-60 minutes. Harvest and test as described above, the result is described in FIG. 8A. In another experiment, 60 minute (RT or 37 C) incubation with 0.01% PLL is compared to 120 minute incubation (RT). Harvest and test as described above, the result is described in FIG. 8B.

Example 13

Transfection Mixture

Experimentation has been performed to determine if additional molar equivalents of Rev increases the titer of lentiviral vector produced using calcium-phosphate transfection.

HEK 293T cells were seeded at 5E4 cells/cm$^2$ on a Friday and allowed to expand over the weekend in DMEM, GLUTAMAX™ (L-glutamine cell culture supplement), FBS (10%), and 1% Sodium Pyruvate. The cells were harvested on Monday.

A five-day procedure for transfection and harvesting transfected cells is described below:
Day 1: Poly L-Lysine coat 12 T-75 culture flasks. Harvest cells, count, and calculate the volume of cell suspension required for $4 \times 10^7$ total cells. Place the volume of cell suspension required for $4 \times 10^7$ total cells into the first flask of each set of 6 duplicates. Add DMEM media containing GLUTAMAX™ (L-glutamine cell culture supplement), FBS (10%), and 1% Sodium Pyruvate to each flask to a final volume of 34 mL. Prepare each of the six transfection mixtures as above. Incubate at RT for 20 minutes. Add chloroquine to the cells just after 20 minutes incubation of the transfection mixture. Add the 2 mL of transfection mixture to each appropriate flask containing the cells and chloroquine. Aliquot 18 mL of cell suspension/chloroquine/transfection mix to the duplicate T-75 flask.

Day 2: Perform Media change. Remove the supernatant from each flask. Add ULTRACULTURE™ (general purpose, serum free medium) to each flask 18 mL. Incubate at 37° C., 5% CO$_2$ for 24 hours.

Day 3: Perform Media change and Harvest #1. Remove supernatant from each flask. Set aside. Add ULTRACULTURE™ (general purpose, serum free medium) to each flask. Incubate at 37° C., 5% CO$_2$ for 24 hours, 0.45 µm filter the supernatant and aliquot five 3 mL samples. Freeze all aliquots.

Day 4: Perform Media change and Harvest #2. Remove supernatant from each flask. Set aside. Add ULTRACULTURE™ (general purpose, serum free medium) 18 mL to each flask. Incubate at 37° C., 5% $CO_2$ for 24 hours, 0.45 µm filter the supernatant and aliquot five 3 mL samples. Freeze all aliquots.

Day 5: Perform Media change and Harvest #3. Remove supernatant from each flask, 0.45 µm filter the supernatant and aliquot five 3 mL samples. Freeze all aliquots.

Figure 9A:
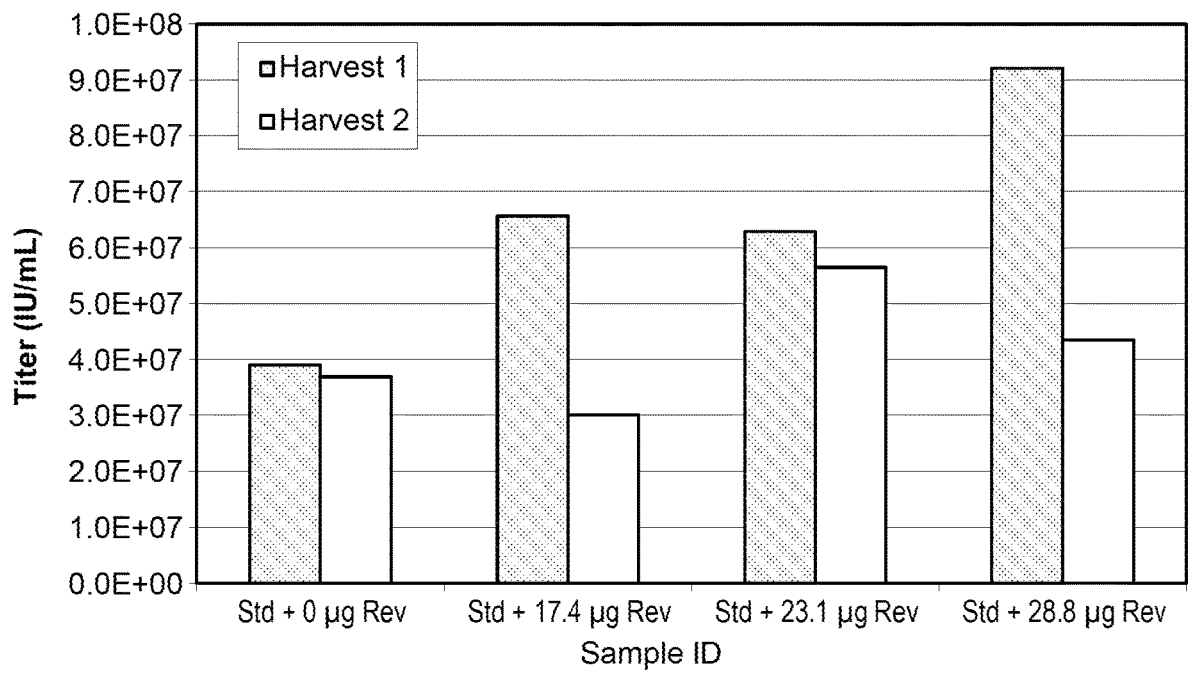
FIG. 9 depicts an experimentation examining the impact of variable amounts of additional RSV Rev plasmid content of the transfection mixture on titers of lentiviral vector, concentrated via ultracentrifugation. Normalized viral titers and total infectious units for each transfection condition were plotted in (A) and (B).
Figure 9B:
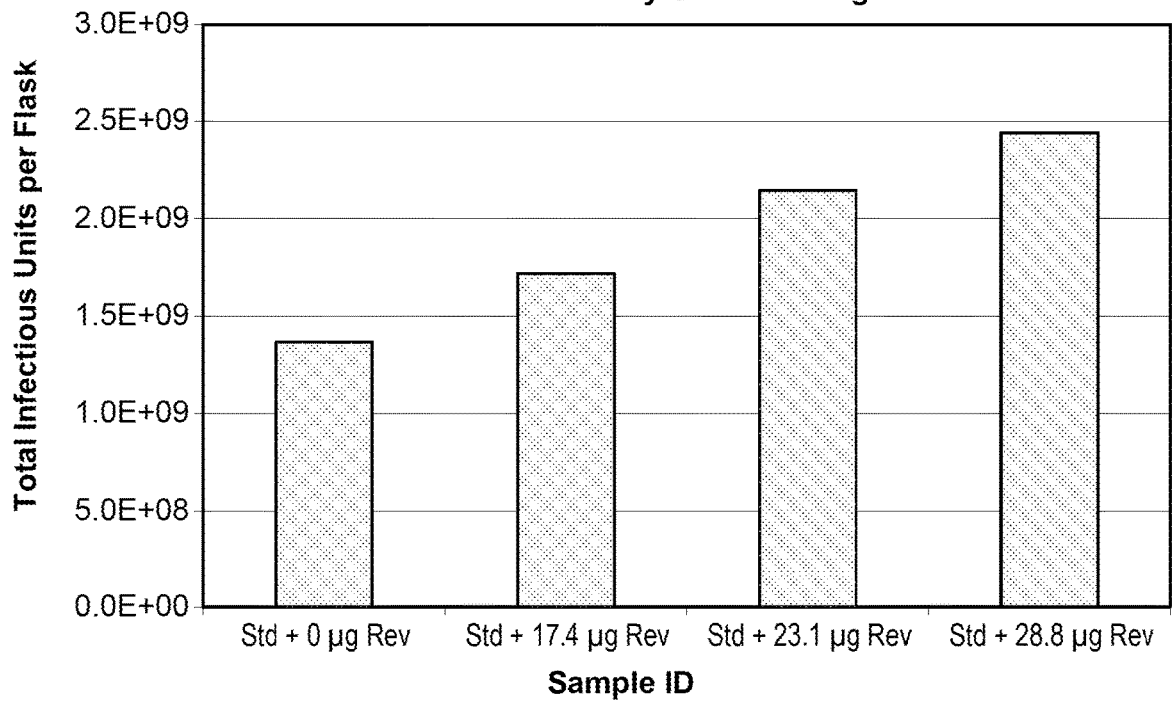

The experimental results are shown in FIGS. 9A and 9B The data from this experimentation suggests that adding additional molar equivalents of Rev increases the titer of lentiviral vector produced using calcium-phosphate transfection.

Example 14

Transfection Cell Density

Experimentation has been performed to compare several cell densities for 293T cells at transfection. Seeding densities were based on T225s, but were scaled down to T75 scale for this experiment. Densities included:
$7 \times 10^7$ cells/T225 ($2.33 \times 10^7$ cells/T75)
$6 \times 10^7$ cells/T225 ($2.00 \times 10^7$ cells/T75)
$5 \times 10^7$ cells/T225 ($1.67 \times 10^7$ cells/T75)
$4 \times 10^7$ cells/T225 ($1.33 \times 10^7$ cells/T75)
$3 \times 10^7$ cells/T225 ($1.00 \times 10^7$ cells/T75)
The experimental procedure is described below.

293T cells were seeded four days prior to transfection at $5 \times 10^4$ cells/cm². 15 T75 flasks were treated with poly-L-lysine at least one hour at 37° C., 5% $CO_2$. 293T cells were harvested. Conditioned media was collected, 0.45 µm filtered, and held at 4° C. One cell/D10/chloroquine mix was prepared for each of the 5 cell densities. One DNA/$H_2O$/$CaCl_2$/2×HBS mix was prepared for all flasks in the experiment and distributed over the cell mixes. After approximately 16-19 hours of incubation at 37° C., 5 $CO_2$, cells were re-fed with at least 50% conditioned media/50% fresh warm D10. Approximately 16 hours before Harvest 1, each flask was treated with 50 Units/mL benzonase and 10 mMolar $MgCl_2$. Supernatant was harvested from each flask, 0.45 µm filtered, and aliquots prepared for testing and frozen at −80° C. Flasks were re-fed. Approximately 24 hours after Harvest 1, a second harvest was performed as above. Aliquots were prepared for testing and frozen at −80° C. Infectious titers were measured on MEL cells. The experimental results are shown in FIG. 10.

The data from this experimentation suggests that the practice of plating 60 million 293T cells per T225 at transfection is optimal.

Example 15

Transfection Vessel and Gassing

Experimentation has been performed to compare transfection in CORNING® 5-stacks vs. 10-stacks transfection vessels and to evaluate the effect of treating the vessels with 5% $CO_2$ at transfection and re-feeds. The experimental procedure is described below:

293T cells were seeded at $5 \times 10^4$ cells/cm² four days prior to transfection. 5-stacks and 10-stacks were pre-equilibrated at 37° C., 5% $CO_2$ overnight. 293T cells were harvested, and conditioned media was collected, 0.45 µm filtered, and stored at 4° C. Cells were transfected with GbG (VSV-G) and seeded in D10. A master mix of DNA/water was prepared and split over the four transfection vessels. Appropriate vessels were then treated with gas prior to incubation at 37° C., 5% $CO_2$. The following morning, transfection mix was removed and each stack was fed with at least 50% conditioned media/50% fresh D10. Appropriate vessels were gassed prior to continuing incubation. Approximately 16 hours before the first harvest, 50 Units/mL benzonase and 10 mMolar $MgCl_2$ was added to stacks. Appropriate vessels were gassed prior to continuing incubation. Supernatant was harvested from each vessel, 0.45 µm filtered, and aliquots were frozen at −80° C. for testing. Stacks were re-fed and appropriate vessels gassed prior to continued incubation. Approximately 24 hours after Harvest 1, a second harvest was performed as in the above. The experimental results are shown in FIGS. 11A to 11B.

The results demonstrate that 5-stacks produced higher titers than 10-stacks. When the difference in scale between 5 and 10-stacks was considered (FIG. 11B), 5-stacks still produced 2-3 fold more virus. This may be explained by better gas exchange in 5-stacks, and by easier/more effective mixing and distribution of reagents in the 5-stacks. In both the 5 and 10-stack arms, gassing of flasks seems to confer an advantage.

Example 16

Gassing

Figure 12:
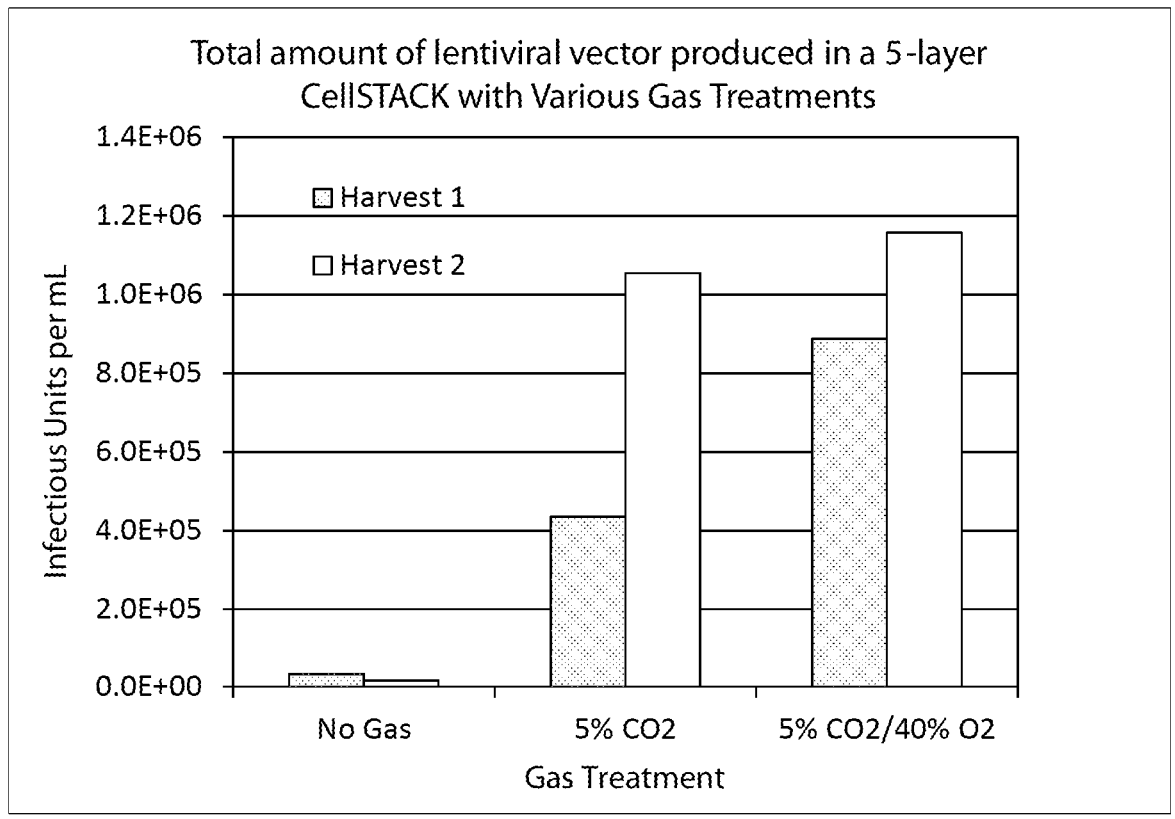
FIG. 12 depicts an experimentation examining the impact of treating transfection vessels with $CO_2$, or with $CO_2$ and $O_2$, on the total amount of lentiviral vector produced in a 5-layer CELLSTACK™ (stacked culture vessel). Total infectious units of virus for each harvest of transfected cells are plotted.

Experimentation has been performed to compare the effect of treating vessels with 1) no gas; 2) 5% $CO_2$; and 3) 5% $CO_2$/40% $O_2$. The experimental procedure is described below:

293T cells were seeded four days prior to the anticipated date of transfection at $5 \times 10^4$ cells/cm². Due to a delay in receiving one of the gases, the cells were split on the anticipated transfection day and the day after that. Cells were used 6 days after initial seeding. 3 5-stacks were pre-equilibrated overnight at 37° C., 5% $CO_2$. 293T cells were harvested, and conditioned media was collected, 0.45 µm filtered, and stored at 4° C. overnight. Cells were transfected and seeded in D10. A master mix of DNA/$H_2O$ was prepared and then split into thirds. Separately, each third was combined with $CaCl_2$ and 2×HBS, incubated approximately 20 minutes at room temperature, and plated in cell stacks. Appropriate stacks were treated with gas. Approximately 16-19 hours after transfection, the cells were re-fed with at least 50% conditioned media and 50% D10. Appropriate stacks were treated with gas, and incubation was continued. 16 hours before Harvest 1, flasks were treated with 50 U/mL benzonase and 10 mMolar $MgCl_2$. Appropriate stacks were treated with gas, and incubation was continued. Approximately 24 hours after media change, supernatant was harvested from each vessel, passed through a leukocyte reducing filter (LRF), and aliquots prepared for testing. Each vessel was re-fed, and appropriate vessels were treated with gas before continuing incubation. Approximately 24 hours after first harvest, supernatant from each vessel was harvested a second time, passed through a LRF, and aliquots prepared for testing. Infectious titers were measured on MEL cells. The experimental results are shown in FIG. 12.

The data from this experimentation suggests that gassing is beneficial, and that the 5% $CO_2$/40% $O_2$ mix was more helpful than 5% $CO_2$ alone when using CELLSTACK™ (stacked culture vessel).

Example 17

Gassing

Experimentation has been performed to compare the effect of treating vessels with the following gas conditions, as in previous gassing experiments. This experiment was done on a smaller scale (T225 scale) to add confidence to previous results. Gassing condition included: 1) no gas; 2) 5% $CO_2$; 3) 5% $CO_2$/40% $O_2$.

The experimental procedure is described below.

Figure 13:
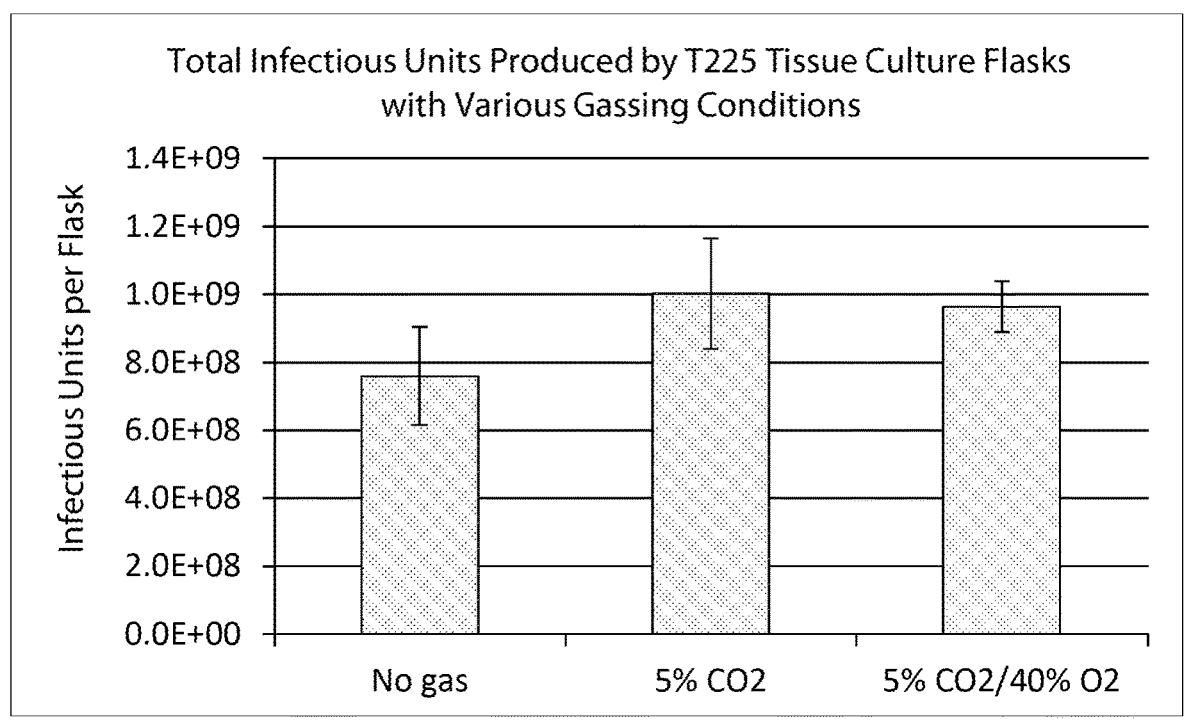
FIG. 13 depicts an experimentation examining the impact of treating transfection vessels with $CO_2$ and $O_2$ on viral production in T225 tissue culture flasks with various gassing conditions. Average infectious units of virus produced by flask under each gassing condition are plotted (triplicate groups).

293T cells were grown for transfection and seeded at $5 \times 10^4$ cells/cm² four days prior to transfection. 293T cells were harvested, and conditioned media was collected, 0.45 μm filtered, at stored at 4° C. A master mix of DNA/H2O was prepared, and then split into thirds. Separately, each third was combined with $CaCl_2$ and 2×HBS, incubated, and added to T225 flasks. Appropriate vessels were gassed as shown below. Cells were re-fed at least 50% conditioned media and 50% fresh D10 for first media change, approximately 16-19 hours after transfection. Appropriate vessels were gassed and incubation continued. Approximately 24 hours after media change, supernatant from each vessel was harvested, 0.45 μm filtered, and aliquots were prepared for testing and frozen. Flasks were re-fed with D10 and appropriate flasks were gassed. Approximately 24 hours after first harvest, a second harvest was performed as above Infectious titers on MEL cells were compared. The experimental results are shown in FIG. 13.

Within this experiment, gassing did show an advantage over non-gassed flasks; yields with gas were approximately 1.3× higher than yields from non-gassed flasks. However, unlike in previous experiments, there was no clear effect of the type of gas mix used when transfecting in T225 flasks.

Example 18

Cell Seeding/Conditioned Media Timing Experiment

Experimentation has been performed to determine the best combination of times for cell seeding pre-transfection and time interval for preparing conditioned media. Cells were harvested either 3 or 4 days after plating. Cells were combined with media that had been conditioned for either 3 or 4 days and transfected (FIG. 14A). Results are shown in FIG. 14B.

The data from this experimentation suggests that cells cultured for 4 days are superior as compared to cells cultured for 3 days and that 4-day conditioned media is equal or better than 3-day conditioned media.

Example 19

Fresh vs Frozen Transfection Mix Comparison

Experimentation has been performed to determine if transfection reagent (plasmid, CaCl2, HBS, and water), prepared ahead of time, diluted 4-fold with D10, and frozen can transfect cells as efficiently as a freshly prepared transfection mixture.

The experimental procedure is described below.

Day 1: Prepare enough transfection mix for 20 T75s. After the 20 minute room temperate incubation, quickly dilute the transfection reagent 4-fold with D10. Aliquot, label, and store half the vials at −20° C. and half at −70° C. at least overnight. Day 2: Thaw frozen aliquots at room temperature and transfect three T75 flasks with each arm as listed in following steps. Prepare fresh transfection reagent. Transfect 3×T75 with fresh transfection reagent. Transfect 3×T75 with transfection reagent that was frozen at −70° C. Transfect 3×T75 with transfection reagent that was frozen at −20° C. Re-feed the following morning, and add 50 U/mL benzonase and 10 mMolar $MgCl_2$ approximately 16 hrs prior to harvest. Collect supernatants from Harvest 1 (only one harvest), 0.45 μm filter, and aliquot. The experimental results are shown in FIG. 15.

The data from this experimentation suggests that freezing of the transfection mix overnight at −70° C. or −20° C. does not adversely affect titer.

Example 20

Fresh vs Frozen Transfection Mix Comparison

Experimentation has been performed to compare the pre-made transfection mix stored at −20° C. and −70° C. with fresh mix and to compare 0, 10, and 20 minute incubations for transfection mix.

The experimental procedure is described below.

On the day before transfection: Enough DNA/water mix for 18 T75 flasks was prepared and divided into thirds. Separately, the mixes were combined with $CaCl_2$ and 2×HBS, then incubated 0, 10, or 20 minutes before being diluted four-fold with D10. Then the combined and diluted mixes were divided in half once more and stored either at −70° C. or −20° C. On the day of transfection: Enough DNA/water mix for 9 T75 flasks was prepared and divided into thirds. Separately, the mixes were combined with $CaCl_2$ and 2×Hbs, then incubated 0, 10, or 20 minutes before being used to transfect 3 T75 flasks per incubation condition. On the day of transfection: Frozen reagents were thawed at room temperature (in water), then used to transfect 18 T75 flasks. Approximately 18 hours after transfection, flasks were re-fed with at least 50% conditioned media from 293T cells and 50% fresh D10. Approximately 16 hours before harvest, flasks were treated with 50 U/mL benzonase and 10 mMolar $MgCl_2$. Supernatants were collected, 0.45 μm filtered, and aliquots frozen at −80° C. Samples were analyzed for infectious titer on MEL cells. The experimental results are shown in FIG. 16.

The data from this experimentation suggests that pre-making transfection mix and storing overnight at −70° C. or −20° C. does not negatively affect viral yield; results are similar to fresh mix. In the two pre-frozen groups, 0, 10, or 20 minute incubations of transfection mix do not seem to affect results. Only for the fresh group does a 20 minute incubation show an increased titer.

Example 21

Comparison of Temperature of Cells/CCM for Lenti Transfection

Experimentation has been performed to determine if incubating the CCM-Cell Suspension at 37 C before introducing the Transfection Mix will affect the titer.

The experimental procedure is described below.

Seeded 293T cells four days prior to transfection at $5 \times 10^4$ cells/cm². Harvested 293T cells and collect conditioned media. Stored filtered conditioned media at room temperature overnight. Prepared one bottle of cell suspension in D10, then divided into two bottles labeled "37° C." and "RT". Left bottles at indicated temperature for approximately one hour before starting transfection step. Pre-treated six T75 flasks with 0.1% sterile-filtered Poly-L-Lysine. Transfected and seeded six T-75 flasks in D10. Prepared one large Transfection Mix, and added appropriate amount to each temperature-controlled bottle of Cell Suspension. Without delay, pipetted 18 mL from the "37 C" bottle into each of three T75 bottle (37 C group) and without letting the flasks cool down immediately placed flasks into the incubator. Repeated for the "RT" bottle and remaining three flasks (Room Temp group). Incubated flasks overnight in VPF. No gassing was used in this experiment. The next morning re-fed cells with at least 50% conditioned media/ 50% fresh D10 at room temperature. Added 50 Units/mL Benzonase and 10 mMolar $MgCl_2$ approximately 16 hours pre-harvest. Re-incubated at 37° C./5% $CO_2$. Harvest 1: Approximately 24 hours after Media Change, harvested supernatant from each vessel, 0.45 µm filtered, and aliquots were prepared for testing and frozen at −80° C. Flasks re-fed and re-incubated. Harvest 2: Approximately 24 hours after first harvest, harvested supernatant from each flask, 0.45 µm filtered, and aliquots were prepared for testing and frozen at −80° C. Infectious titers were measured on MEL cells. The experimental results are shown in FIG. 17.

The data from this experimentation suggests that cell suspension incubated at 37° C. before transfection performs at least as well as or slightly better than cell suspension held at room temperature.

Example 22

Plasmid Comparison

Experimentation has been performed to compare titer of supernatant produced with 3 lots of plasmid: GbG vector from Puresyn (A, D), GbG vector from Plasmid Factory (B), and GbGm plasmid from Puresyn (C) and to compare the effect of a 20-minute incubation of transfection reagents vs. no incubation (A versus D).

The experimental procedure is described below.

293T cells were seeded at $5 \times 10^4$ cells/$cm^2$ four days prior to transfection. 293T cells were harvested, and conditioned media was collected, 0.45 µm filtered, and stored at 4° C. Cells were transfected and seeded in D10 per 19 A. DNA/ Water/2.5M $CaCl_2$/2×HBS mixtures were incubated either for 20 minutes at room temperature before plating, or not incubated and plated immediately. Approximately 16-19 hours after transfection, cells were re-fed with 50% fresh D10/at least 50% conditioned media. Approximately 16 hours before Harvest 1, flasks were treated with 50 U/mL benzonase and 10 mMolar $MgCl_2$. Approximately 24 hours after media change, supernatants were harvested, 0.45 µm filtered, and stored at 4° C. A second harvest was performed approximately 48 hours after media change. Aliquots of each harvest were tested for infectious titer on MEL cells. The experimental results are shown in FIG. 18.

The data from this experimentation suggests that similar yields of virus were produced by GbG from PureSyn, GbG from Plasmid Factory, and GbGm from PureSyn and that a 20 minute incubation of DNA cocktail prior to plating can be beneficial.

Example 23

Sodium Chloride Adjustment Timing

For the GMP production of GbGm (VSV-G), unconcentrated supernatant must be adjusted to 300 mMolar NaCl before loading on MUSTANG® Q anion-exchange chromatography capsules. Experimentation has been performed to investigate the effect on infectious titer when this adjustment was made the day before purification.

The experimental procedure is described below.

Figure 19:
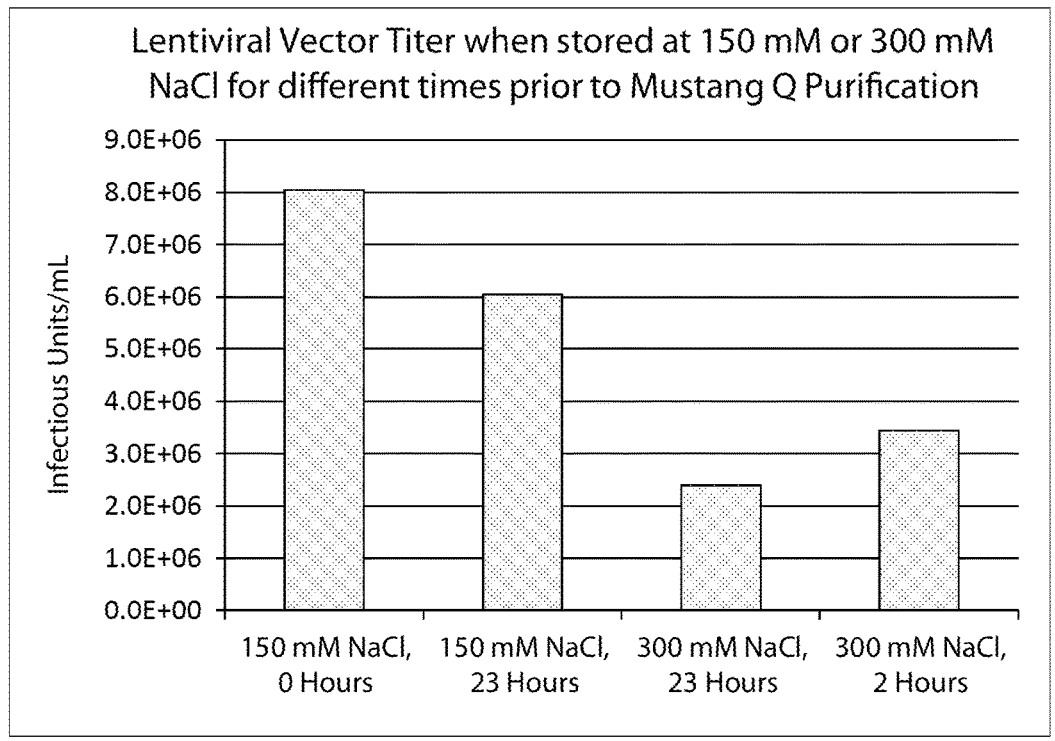
FIG. 19 depicts an experimentation examining the impact on infectious lentiviral vector titer when sodium chloride adjustment from 150 to 300 mMolar is made the day before virus purification via MUSTANG® Q anion-exchange chromatography. Infectious titers of supernatant with adjusted salt concentrations for different time periods are plotted.

A pool of freshly-harvested GbGm supernatant was designated for this experiment. Immediately after harvest, a sample was removed from the pool, 0.45 µm filtered, and frozen in aliquots. A second sample of the pool was held at ambient temperature overnight. After approximately 23 hours, this sample was 0.45 µm filtered and frozen in aliquots (Group 150 mMolar NaCl, 0 hours). A 20 mL sample of the pool was removed and set aside for 23 hours (Group 150 mMolar NaCl, 23 hours). For the third group, the sodium chloride concentration was adjusted from 150 mMolar to 300 mMolar by adding 5M NaCl. The sample was inverted several times to mix, then held at ambient temperature overnight (Group 300 mMolar NaCl, 23 hours). After approximately 23 hours, this sample was 0.45 µm filtered and frozen in aliquots. After incubation of the pool at ambient temperature overnight (approximately 23 hours), a separate 20 mL sample was removed the following day and adjusted to 300 mMolar NaCl by addition of 5M NaCl. This sample was inverted several times to mix, then held at ambient temperature for approximately 2 hours (Group 300 mMolar NaCl, 2 hours). Then the sample was 0.45 µm filtered and frozen in aliquots. The experimental results are shown in FIG. 19.

The experiment demonstrates that approximately 25% of original titer is lost when the supernatant is held at ambient temperature overnight without any salt adjustment. Comparing the second and third group shows that exposure to 300 mMolar NaCl during the overnight ambient temperature hold results in a loss of about 60% of the titer, compared to an unadjusted sample also incubated at ambient temperature overnight. Comparing the third and fourth group, limiting the exposure to 300 mMolar NaCl to about 2 hours before MUSTANG® Q anion-exchange purification results in the least loss of titer of approximately 43%. This indicates that exposure to 300 mMolar NaCl should be kept as short as possible.

Example 24

Comparison of PS and PES Membranes and Use of Bubbles for Vector Harvest from TFF Experimentation has been performed to compare two PS columns, with/without air bubbles and a PES vs PS membrane (both without bubbles). In this run, a small amount of air had entered the TFF system during final phase.

The experimental procedure is described below.

A total volume 3 Liters of lentiviral vector supernate was thawed overnight at ambient temperature and completed thawing at 37° C. the morning of use. Concentration of NaCl was adjusted to 300 mMolar, and the product was run through a 0.45 µm Gamma-Gold filter. 3 Liters of supernatant was run through the MUSTANG® Q anion-exchange filter as follows: The filter was sanitized using 25 mL 1 M NaOH at 10 mL/min+30 minute hold; washed using 25 mL 1 M NaCl at 10 mL/min; equilibrated using 200 mL 25 mMolar Tris-HCl (pH 8.0), 150 mMolar NaCl at 50 mL/min; and loaded with 3000 mL of vector adjusted to 300 mMolar NaCl. The filter was washed with 200 mL of 25 mMolar Tris-HCl (pH 8.0), 150 mMolar NaCl at 50 mL/min, and the product was eluted with 100 mL of 1.2 M NaCl, 25 mMolar Tris-HCl (pH 8.0). After elution, 100 mL 25 mMolar Tris-HCl (pH 8.0) was immediately added to dilute the salt for a total volume of 200 mL. Final, the product was diluted with 400 mL of 25 mMolar Tris-HCl (pH 8.0) and 150 mMolar NaCl to increase the volume to 600 mL for 3 runs on TFF columns at 200 mL starting volume for each.

Figures 21A, 21B:
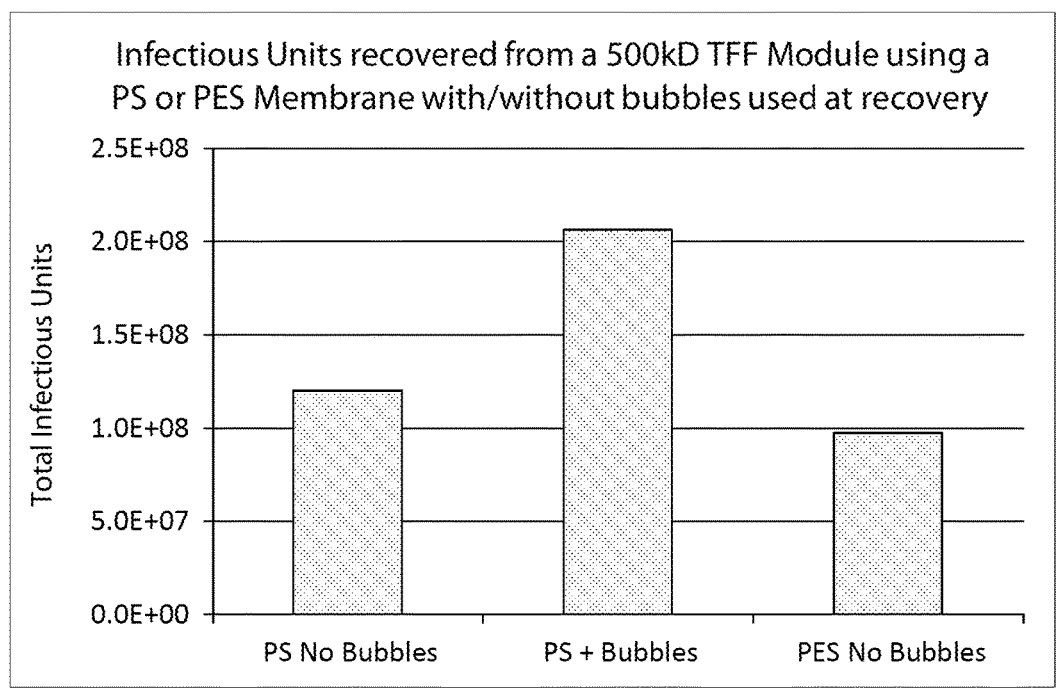
FIG. 21 depicts an experimentation comparing the efficiency of recovering infectious particles using PS and PES TFF modules with and without air bubbles entering the TFF system during the final phase. Experimental conditions are shown in (A); total normalized infectious units of virus produced by PS and PES TFF modules with and without bubbles used at recovery are plotted in (B).

200 mL of diluted sample was run through each of three TFF columns as indicated below: Rinse each module with 500 mL 20% ethanol; rinse each module with 300 mL 25 mMolar Tris-HCl (pH 8.0) and 150 mMolar NaCl; run 200 mL product and concentrate; add 200 mL of X-VIVO 10 (chemically defined, serum free hematopoietic cell medium) media to diafilter. The TFF profile from one of the runs shows stable pressures during the concentration step as depicted in FIG. 20. The experimental design is summarized in FIG. 21A. The experimental results are shown in FIG. 21B.

The data from this experimentation suggests that when comparing the two materials, PS performed slightly better (1.2×) than PES using a trans-membrane pressure of 5-6 psi and shear of 5000 to 6000 $s^{-1}$. Comparing the two PS modules, the "+ bubbles" module performed 1.7× better than the module without bubbles.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the specific number of genes in a screening panel or targeted by a therapeutic product, the type of gene(s), the type of genetic disease or deficiency, and the particular gene(s) specified. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

All references cited herein are incorporated by reference in their entirety as though fully set forth. Also incorporated herein by reference in their entirety are: 1) Baum, C., S. Hegewisch-Becker, H. G. Eckert, C. Stocking, and W. Ostertag. 1995. Novel retroviral vectors for efficient expression of the multidrug resistance (mdr-1) gene in early hematopoietic cells. *J Virol* 69:7541-7547; 2) Boussif, O., F. Lezoualc'h, M. A. Zanta, M. D. Mergny, D. Scherman, B. Demeneix, and J. P. Behr. 1995. A versatile vector for gene and oligonucleotide transfer into cells in culture and in vivo: polyethylenimine. *Proc Natl Acad Sci USA* 92:7297-7301; 3) Cornetta, K., L. Matheson, and C. Ballas. 2005. Retroviral vector production in the National Gene Vector Laboratory at Indiana University. *Gene Ther* 12 Suppl 1:S28-35; 4) Dull, T., R. Zufferey, M. Kelly, R. J. Mandel, M. Nguyen, D. Trono, and L. Naldini. 1998. A third-generation lentivirus vector with a conditional packaging system. *J Virol* 72:8463-8471; 5) Felgner, P. L., T. R. Gadek, M. Holm, R. Roman, H. W. Chan, M. Wenz, J. P. Northrop, G. M. Ringold, and M. Danielsen. 1987. Lipofection: a highly efficient, lipid-mediated DNA-transfection procedure. *Proc Natl Acad Sci USA* 84:7413-7417; 6) Feng, Y., Z. Liu, H. Cao, X. Meng, Z. Qu, M. Xiong, and Z. Deng. 2004. Construction of eukaryotic expression plasmid of human PRX3 and its expression in HEK-293FT cells. *J Huazhong Univ Sci Technolog Med Sci* 24:311-313, 321; 7) Food and Drug Administration. 2001. Guidance for human somatic cell therapy and gene therapy. *Hum Gene Ther* 12:303-314; 8) Geraerts, M., M. Michiels, V. Baekelandt, Z. Debyser, and R. Gijsbers. 2005. Upscaling of lentiviral vector production by tangential flow filtration. *J Gene Med* 7:1299-1310; 9) Graham, F. L., and A. J. van der Eb. 1973. A new technique for the assay of infectivity of human adenovirus 5 DNA. *Virology* 52:456-467; 10) Grez, M., E. Akgun, F. Hilberg, and W. Ostertag. 1990. Embryonic stem cell virus, a recombinant murine retrovirus with expression in embryonic stem cells. *Proc Natl Acad Sci USA* 87:9202-9206; 11) Hacein-Bey-Abina, S., C. Von Kalle, M. Schmidt, M. P. McCormack, N. Wulffraat, P. Leboulch, A. Lim, C. S. Osborne, R. Pawliuk, E. Morillon, R. Sorensen, A. Forster, P. Fraser, J. I. Cohen, G. de Saint Basile, I. Alexander, U. Wintergerst, T. Frebourg, A. Aurias, D. Stoppa-Lyonnet, S. Romana, I. Radford-Weiss, F. Gross, F. Valensi, E. Delabesse, E. Macintyre, F. Sigaux, J. Soulier, L. E. Leiva, M. Wissler, C. Prinz, T. H. Rabbitts, F. Le Deist, A. Fischer, and M. Cavazzana-Calvo. 2003. LMO2-associated clonal T cell proliferation in two patients after gene therapy for SCID-X1. *Science* 302:415-419; 12) Hanenberg, H., X. L. Xiao, D. Dilloo, K. Hashino, I. Kato, and D. A. Williams. 1996. Colocalization of retrovirus and target cells on specific fibronectin fragments increases genetic transduction of mammalian cells. *Nature Medicine* 2:876-882; 13) Herbst, F., C. R. Ball, O. Zavidij, S. Fessler, M. Schmidt, H. Veelken, C. von Kalle, and H. Glimm. 2011. 10-Year stability of clinical-grade serum-free gamma-retroviral vector-containing medium. *Gene Ther* 18:210-212; 14) Higashikawa, F., and L. Chang. 2001. Kinetic analyses of stability of simple and complex retroviral vectors. *Virology* 280:124-131; 15) Hildinger, M., K. L. Abel, W. Ostertag, and C. Baum. 1999. Design of 5' untranslated sequences in retroviral vectors developed for medical use. *J Virol* 73:4083-4089; 16) Howe, S. J., M. R. Mansour, K. Schwarzwaelder, C. Bartholomae, M. Hubank, H. Kempski, M. H. Brugman, K. Pike-Overzet, S. J. Chatters, D. de Ridder, K. C. Gilmour, S. Adams, S. I. Thornhill, K. L. Parsley, F. J. Staal, R. E. Gale, D. C. Linch, J. Bayford, L. Brown, M. Quaye, C. Kinnon, P. Ancliff, D. K. Webb, M. Schmidt, C. von Kalle, H. B. Gaspar, and A. J. Thrasher. 2008. Insertional mutagenesis combined with acquired somatic mutations causes leukemogenesis following gene therapy of SCID-X1 patients. *J Clin Invest* 118:3143-3150; 17) Jordan, M., and F. Wurm. 2004. Transfection of adherent and suspended cells by calcium phosphate. *Methods* 33:136-143; 18) Karolewski, B. A., D. J. Watson, M. K. Parente, and J. H. Wolfe. 2003. Comparison of transfection conditions for a lentivirus vector produced in large volumes. *Hum Gene Ther* 14:1287-1296; 19) Kraunus, J., D. H. Schaumann, J. Meyer, U. Modlich, B. Fehse, G. Brandenburg, D. von Laer, H. Klump, A. Schambach, J. Bohne, and C. Baum. 2004. Self-inactivating retroviral vectors with improved RNA processing. *Gene Ther* 11:1568-1578; 20) Loew, R., Y. Meyer, K. Kuehlcke, L. Gama-Norton, D. Wirth, H. Hauser, S. Stein, M. Grez, S. Thornhill, A. Thrasher, C. Baum, and A. Schambach. 2010. A new PG13-based packaging cell line for stable production of clinical-grade self-inactivating gamma-retroviral vectors using targeted integration. *Gene Ther* 17:272-280; 21) Merten, O. W. 2004. State-of-the-art of the production of retroviral vectors. *J Gene Med* 6 Suppl 1:S105-124; 22) Merten, O. W., S. Charrier, N. Laroudie, S. Fauchille, C. Dugue, C. Jenny, M. Audit, M. A. Zanta-Boussif, H. Chautard, M. Radrizzani, G. Vallanti, L. Naldini, P. Noguiez-Hellin, and A. Galy. 2011. Large-scale manufacture and characterization of a lentiviral vector produced for clinical ex vivo gene therapy application. *Hum Gene Ther* 22:343-356; 23) Merten, O. W., P. E. Cruz, C. Rochette, C. Geny-Fiamma, C. Bouquet, D. Goncalves, O. Danos, and M. J. Carrondo. 2001. Comparison of different bioreactor systems for the production of high titer retroviral vectors. *Biotechnol Prog* 17:326-335; 24) Modlich, U., J. Bohne, M. Schmidt, C. von Kalle, S. Knoss, A. Schambach, and C. Baum. 2006. Cell-culture assays reveal the importance of retroviral vector design for insertional genotoxicity. *Blood* 108:2545-2553; 25) Montini, E., D. Cesana, M. Schmidt, F. Sanvito, M. Ponzoni, C. Bartholomae, L. Sergi Sergi, F. Benedicenti, A. Ambrosi, C. Di Serio, C. Doglioni, C. von Kalle, and L. Naldini. 2006. Hematopoietic stem cell gene transfer in a tumor-prone mouse model uncovers low genotoxicity of lentiviral vector integration. *Nat Biotechnol* 24:687-696; 26) Naldini, L., U. Blomer, F. H. Gage, D. Trono, and I. M. Verma. 1996. Efficient transfer, integration, and sustained long-term expression of the transgene in adult rat brains injected with a lentiviral vector. *Proc Natl Acad Sci USA* 93:11382-11388; 27) Nordling, D., A. Kaiser, and L. Reeves. 2009. Release testing of retroviral vectors and gene-modified cells. *Methods Mol Biol* 506:265-279; 28) Peng, Z. 2005. Current status of gendicine in China: recombinant human Ad-p53 agent for treatment of cancers. *Hum Gene Ther* 16:1016-1027; 29) Persons, D. A., and C. Baum. 2011. Solving the problem of gamma-retroviral vectors containing long terminal repeats. *Mol Ther* 19:229-231; 30) Pierce, L. N., and P. W. Shabram. 2004. Scalability of a disposable bioreactor from 25 L-500 L run in perfusion mode with a CHO-based cell line: A tech review. Bioprocessing Journal 3; 31) Przybylowski, M., A. Hakakha, J. Stefanski, J. Hodges, M. Sadelain, and I. Riviere. 2006. Production scale-up and validation of packaging cell clearance of clinical-grade retroviral vector stocks produced in cell factories. *Gene Ther* 13:95-100; 32) Reeves, L., P. Smucker, and K. Cornetta. 2000. Packaging cell line characteristics and optimizing retroviral vector titer: the National Gene Vector Laboratory experience. *Hum Gene Ther* 11:2093-2103; 33) Sastry, L., Y. Xu, R. Cooper, K. Pollok, and K. Cornetta. 2004. Evaluation of plasmid DNA removal from lentiviral vectors by benzonase treatment. *Hum Gene Ther* 15:221-226; 34) Schambach, A., J. Bohne, S. Chandra, E. Will, G. P. Margison, D. A. Williams, and C. Baum. 2006. Equal potency of gammaretroviral and lentiviral SIN vectors for expression of O6-methylguanine-DNA methyltransferase in hematopoietic cells. *Mol Ther* 13:391-400; 35) Schambach, A., M. Galla, T. Maetzig, R. Loew, and C. Baum. 2007. Improving transcriptional termination of self-inactivating gamma-retroviral and lentiviral vectors. *Mol Ther* 15:1167-1173; 36) Schambach, A., D. Mueller, M. Galla, M. M. Verstegen, G. Wagemaker, R. Loew, C. Baum, and J. Bohne. 2006. Overcoming promoter competition in packaging cells improves production of self-inactivating retroviral vectors. *Gene Ther* 13:1524-1533; 37) Schambach, A., W. S. Swaney, and J. C. M. van der Loo. 2009. Design and production of retro- and lentiviral vectors for gene expression in hematopoietic cells. In Methods in Molecular Biology. C. Baum, editor Humana Press, Totowa, N. J. 191-205; 38) Schleef, M., and T. Schmidt. 2004. Annimal-free production of ccc-supercoiled plasmids for research and clinical application. *J Gene Med* 6:S45-S53; 39) Segura, M. M., A. Gamier, and A. Kamen. 2006. Purification and characterization of retrovirus vector particles by rate zonal ultracentrifugation. *J Virol Methods* 133:82-91; 40) Segura, M. M., A. Kamen, and A. Gamier. 2006. Downstream processing of oncoretroviral and lentiviral gene therapy vectors. *Biotechnol Adv* 24:321-337; 41) Segura, M. M., A. Kamen, P. Trudel, and A. Gamier. 2005. A novel purification strategy for retrovirus gene therapy vectors using heparin affinity chromatography. *Biotechnol Bioeng* 90:391-404; 42) Thornhill, S. I., A. Schambach, S. J. Howe, M. Ulaganathan, E. Grassman, D. Williams, B. Schiedlmeier, N. J. Sebire, H. B. Gaspar, C. Kinnon, C. Baum, and A. J. Thrasher. 2008. Self-inactivating gammaretroviral vectors for gene therapy of X-linked severe combined immunodeficiency. *Mol Ther* 16:590-598; 43) Throm, R. E., A. A. Ouma, S. Zhou, A. Chandrasekaran, T. Lockey, M. Greene, S. S. De Ravin, M. Moayeri, H. L. Malech, B. P. Sorrentino, and J. T. Gray. 2009. Efficient construction of producer cell lines for a SIN lentiviral vector for SCID-X1 gene therapy by concatemeric array transfection. *Blood* 113:5104-5110; 44) Wikstrom, K., P. Blomberg, and K. B. Islam. 2004. Clinical grade vector production: analysis of yield, stability, and storage of gmp-produced retroviral vectors for gene therapy. *Biotechnol Prog* 20:1198-1203; 45) Williams, D. A., and C. Baum. 2003. Medicine. Gene therapy—new challenges ahead. *Science* 302:400-401; 46) Wilson, J. M. 2005. Gendicine: the first commercial gene therapy product. *Hum Gene Ther* 16:1014-1015; 47) Wright, J. F. 2009. Transient transfection methods for clinical adeno-associated viral vector production. *Hum Gene Ther* 20:698-706; 48) Wu, S. C., G. Y. Huang, and J. H. Liu. 2002. Production of retrovirus and adenovirus vectors for gene therapy: a comparative study using microcarrier and stationary cell culture. *Biotechnol Prog* 18:617-622; 49) Yu, S. F., T. von Ruden, P. W. Kantoff, C. Garber, M. Seiberg, U. Ruther, W. F. Anderson, E. F. Wagner, and E. Gilboa. 1986. Self-inactivating retroviral vectors designed for transfer of whole genes into mammalian cells. *Proc Natl Acad Sci USA* 83:3194-3198; 50) Zufferey, R., T. Dull, R. J. Mandel, A. Bukovsky, D. Quiroz, L. Naldini, and D. Trono. 1998. Self-inactivating lentivirus vector for safe and efficient in vivo gene delivery. *J Virol* 72:9873-9880; 51) Zychlinski, D., A. Schambach, U. Modlich, T. Maetzig, J. Meyer, E. Grassman, A. Mishra, and C. Baum. 2008. Physiological Promoters Reduce the Genotoxic Risk of Integrating Gene Vectors. *Mol Ther* 16:718-725.

What is claimed is:

1. A high titer transfection-based lentiviral vector production method, comprising:
    seeding mammalian cells at a cell density of at least $5 \times 10^4$ cells/cm$^2$ 4 to 5 days prior to cell harvest and transfection;
    harvesting a confluent population of the seeded cells that have progressed beyond log phase of growth at least 24 hours prior to transfection;
    transfecting the cells by mixing the harvested population with transfection reagents and plasmid DNA comprising a lentiviral vector expression plasmid;
    re-seeding the transfected cells into a culture vessel at a transfection cell density of at least $1.25 \times 10^5$ cells per square centimeter;
    capturing the lentiviral vectors from the cell-free supernatant of the transfected, re-seeded cells using an anion-exchange capsule; and
    concentrating the captured lentiviral vectors using a Polysulfone (PS) or Polyether (PES) tangential-flow filtration (TFF) module, wherein the concentrating step comprises (a) applying a trans-membrane pressure of 5-6 psi, (b) applying a shear of 5000 to 6000 s$^{-1}$ to the TFF module, and (c) introducing air into the TFF module before collecting concentrated viral vectors.

2. The method of claim 1, wherein the cells are transfected by mixing the harvested population with transfection reagents and 9.2 µg/ml of plasmid DNA at the time of re-seeding the cells into the culture vessel.

3. The method of claim 1, wherein the re-seeded cells are fed with a culture media containing at least 50% conditioned media.

4. The method of claim 1, wherein the transfection reagents are incubated at room temperature for 20 minutes before mixing with the harvested population.

5. The method of claim 1, wherein the culture vessel is treated with poly-L-lysine before use.

6. The method of claim 1, wherein the culture vessel is a 5-layer cell stack vessel.

7. The method of claim 1, wherein the plasmid DNA comprises the lentiviral vector expression plasmid in combination with one or more plasmids collectively encoding a viral Gag/Pol gene, a viral Envelop gene, and a viral Rev gene.

8. The method of claim 1, further comprising gassing the culture vessel with 5% $CO_2$ or a mixture of 5% $CO_2$ and 40% $O_2$ for 30 seconds after each post-transfecting step before placing the culture vessel into an incubator.

9. The method of claim 1, wherein the anion-exchange capsule is sanitized with 1 M NaOH, pre-conditioned with 1 M NaCl, and equilibrated with 25 mM Tris-HCl (pH 8.0), 150 mM NaCl prior to viral capture.

10. The method of claim 1, wherein the anion-exchange capsule is rinsed with 25 mM Tris-HCl (pH 8.0), 150 mM NaCl after viral capture.

11. The method of claim 1, wherein the anion-exchange capsule is rinsed with 25 mM Tris-HCl (pH 8.0), 1.2 M NaCl to elute captured viral vector.

12. The method of claim 1, wherein the transfection-based production method is carried out, at least in part, in a bioreactor.

13. The method of claim 1, wherein transfecting the cells comprises, transfecting the cells by mixing the harvested population with transfection reagents and plasmid DNA comprising a lentiviral vector and one or more plasmids encoding a viral Gag/Pol gene, a viral Envelop gene, and a viral Rev gene.

14. The method of claim 1, wherein the mammalian cells are 293T cells, 293F cells, NIH 3T3 cells, HEK293 cells, HT1080 cells, or MEL cells.

* * * * *